(12) United States Patent
Demuth et al.

(10) Patent No.: US 9,167,820 B2
(45) Date of Patent: Oct. 27, 2015

(54) ANTI-BIOFILM COMPOUNDS

(75) Inventors: Donald R. Demuth, Louisville, KY (US); Frederick A. Luzzio, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 14/234,343

(22) PCT Filed: Jul. 20, 2012

(86) PCT No.: PCT/US2012/047635
§ 371 (c)(1),
(2), (4) Date: Jan. 22, 2014

(87) PCT Pub. No.: WO2013/016206
PCT Pub. Date: Jan. 31, 2013

(65) Prior Publication Data
US 2014/0161845 A1    Jun. 12, 2014

Related U.S. Application Data

(60) Provisional application No. 61/510,907, filed on Jul. 22, 2011.

(51) Int. Cl.
| | | |
|---|---|---|
| C07D 413/06 | (2006.01) | |
| C07D 413/10 | (2006.01) | |
| C07D 413/14 | (2006.01) | |
| A01N 43/76 | (2006.01) | |

(52) U.S. Cl.
CPC .............. *A01N 43/76* (2013.01); *C07D 413/06* (2013.01); *C07D 413/10* (2013.01); *C07D 413/14* (2013.01)

(58) Field of Classification Search
CPC combination set(s) only.
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,938,949 A | 7/1990 | Borch et al. | |
| 4,992,478 A | 2/1991 | Geria | |
| 2009/0068120 A1 | 3/2009 | Suga | |

FOREIGN PATENT DOCUMENTS

WO    WO 2009/108716 A2    9/2009

OTHER PUBLICATIONS

Daep, C.A. et al., "Structural Characterization of Peptide-Mediated Inhibition of P. gingivalis Biofilm Formation", *Infect. Immun.* 74 (10), 5756-5762 (2006).
Daep, C.A. et al., "Interaction of P. gingivalis with oral streptococci requires a motif that resembles the eukaryotic nuclear receptor box protein-protein interaction domain", *Infect. Immun.* 76, 3272-3280 (2008).
Daep et al., "Selective substitution of amino acids limits proteolytic cleavage and improves the bioactivity of an anti-biofilm peptide that targets the periodontal pathogen, porphyromonas gingivalis", *Peptides* 31, 2173-2178 (2010).
Daep et al., "Structural Dissection and In Vivo Effectiveness of a Peptide Inhibitor of Porphyromonas gingivalis Adherence to *Streptococcus gordonii*", *Infection and Immunity*, vol. 79 (1), 67-74 (2011).
Loner et al., "Click Scaffolds for the inhibition of *Porphyromonas gingivalis* and *Streptococcus gordonii* biofilm formation" ACS Abstract 130, Denver, Colorado, 1 page, Aug. 28, 2011.
Luzzio, F. A., "The Henry Reaction: Recent examples", *Tetrahedron* 57, 915-945 (2001).
Luzzio et al., "Preparation of Benzoheterocyclic Carbaldehydes", *Tetrahedron Lett.* 50, 580-583 (2009).
Manetsch et al., "In situ click chemistry: enzymes made to their own specifications", *J. Am. Chem. Soc.* 126, 12809-12818 (2004).
Patent Cooperation Treaty, International Searching Authority, Search Report and Written Opinion for PCT/US2012/047635, 9 pages, Sep. 13, 2012.
Wang et al., "Fimbrial proteins of P. gingivalis mediate in vivo virulence and exploit TLR2 and complement receptor 3 to persist in macrophages", *J. Immunol.* 15, 2349-2358 (2007).
Whiting et al., "Inhibitors of HIV-1 protease using in situ click chemistry", *Angew. Chem. Int. Ed.* 45, 1435-1439 (2006).

*Primary Examiner* — Nyeemah A Grazier
(74) *Attorney, Agent, or Firm* — Viksnins Harris & Padys PLLP

(57) ABSTRACT

The present invention provides non-peptide compounds of formula (I) wherein: X is —$(C_1$-$C_8)$alkyl-, aryl or -aryl$(C_1$-$C_8)$alkyl-; Y is —$(C_1$-$C_8)$alkyl- or absent; W is heteroaryl, $(C_3$-$C_7)$carbocycle or aryl, wherein any heteroaryl, $(C_3$-$C_7)$ carbocycle or, aryl of W is optionally substituted with one or more (e.g. 1, 2, 3, 4 or 5) $Z^1$ groups; $R^1$ is $(C_1$-$C_8)$alkyl, $(C_2$-$C_8)$alkenyl, $(C_2$-$C_8)$alkynyl or aryl, wherein aryl is optionally substituted with one or more (e.g. 1, 2, 3, 4 or 5) groups selected from $(C_1$-$C_8)$alkyl, $(C_2$-$C_8)$alkenyl, $(C_2$-$C_8)$ alkynyl, $(C_3$-$C_7)$carbocycle, halo$(C_1$-$C_3)$alkyl, —CN, $NO_2$, halogen, —$OR_a$, —$SR_a$, —$S(O)_2NR_bR_c$, —$NR_bR_c$, —$NR_a$-$COR_d$, —$C(O)R_a$, —$C(O)OR_a$, and —$C(O)NR_bR_c$; $R^2$ is $(C_1$-$C_8)$alkyl, $(C_2$-$C_8)$alkenyl, $(C_2$-$C_8)$alkynyl or aryl, wherein aryl is optionally substituted with one or more (e.g. 1, 2, 3, 4 or 5) groups selected from $(C_1$-$C_8)$alkyl, $(C_2$-$C_8)$ alkenyl, $(C_2$-$C_8)$alkynyl, $(C_3$-$C_7)$carbocycle, halo$(C_1$-$C_3)$ alkyl, —CN, $NO_2$, halogen, —$OR_e$, —$SR_e$, —$S(O)_2NR_fR_g$, —$NR_fR_g$—$NR_eCOR_h$, —$C(O)R_e$, —$C(O)OR_e$ and —$C(O)$ $NR_fR_g$; 1 that mimic the streptococcal; SspB Adherence Region (BAR) and function as inhibitors of *P. gingivalis* adherence to streptococci. The invention also provides methods of making and using the inhibitors.

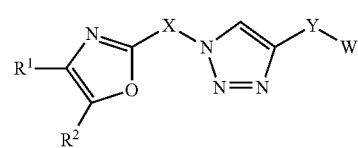

20 Claims, 9 Drawing Sheets

Figure 2

Scheme 1. Structures and Synthesis of Group 1 Pyrimidine-Scaffold Inhibitors

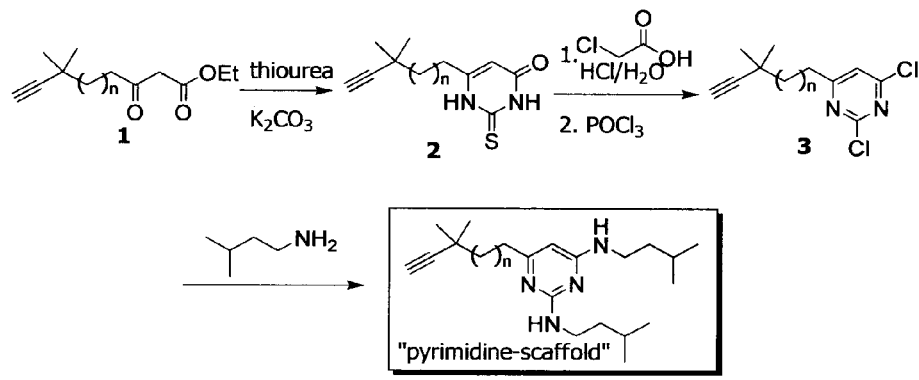

Scheme 2. Structures and Synthesis of Group 1 Triazene-Scaffold Inhibitors

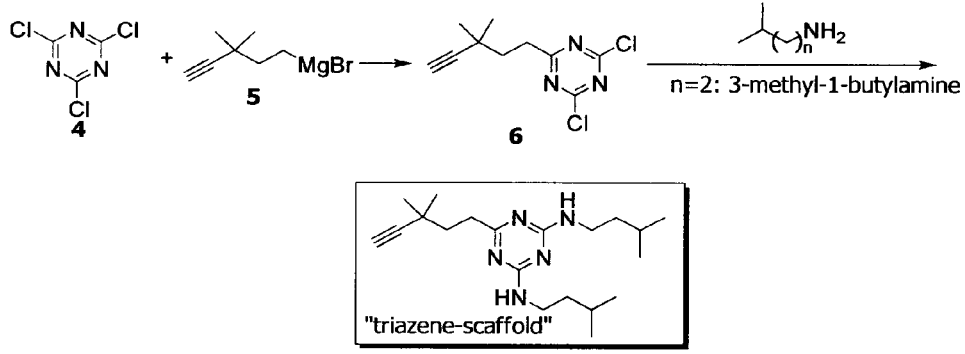

Scheme 3. Structures and Synthesis of Group 1 Cyclohexane-Scaffold Inhibitors

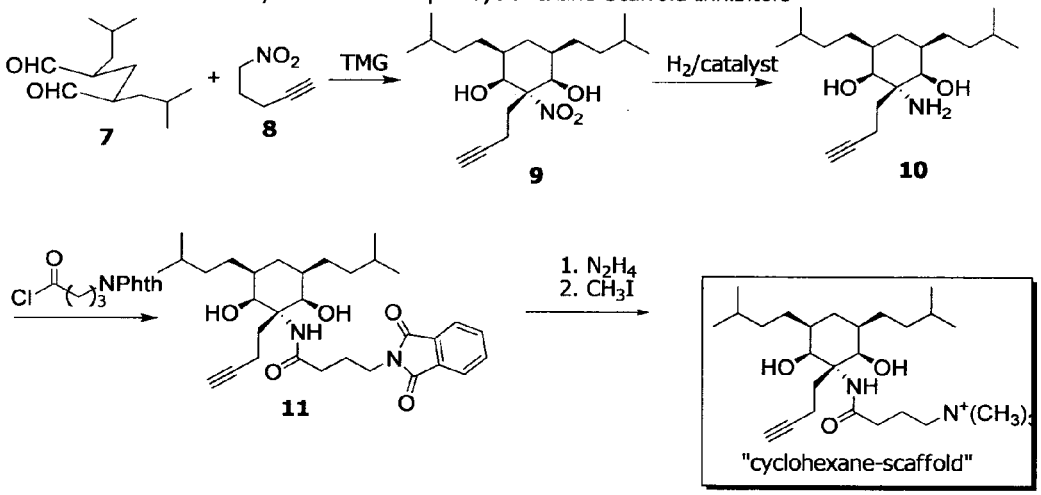

*"double Henry" reaction forms two bonds simultaneously to form a symmetrical six-member ring

*Reduction of the nitrodiol may be done with lithium aluminum hydride or aluminum amalgam as well as $H_2$/catalyst

Scheme 4. Structures and Synthesis of Group 2 Benzoxazole-Scaffold Inhibitors

*The length of the terminal acetylene linker may be varied

Figure 4

|  | N | I | T | V | K |
|---|---|---|---|---|---|
| promotes P. gingivalis adherence | R K H S |  |  | I F W |  |
| detrimental to P. gingivalis adherence | D P G |  |  | D P |  |

Figure 5
Scheme 5. Structures and Synthesis of Oxazole-ine and Oxazole-Based NITVK Motif BAR Inhibitors with the Azide Coupling Component
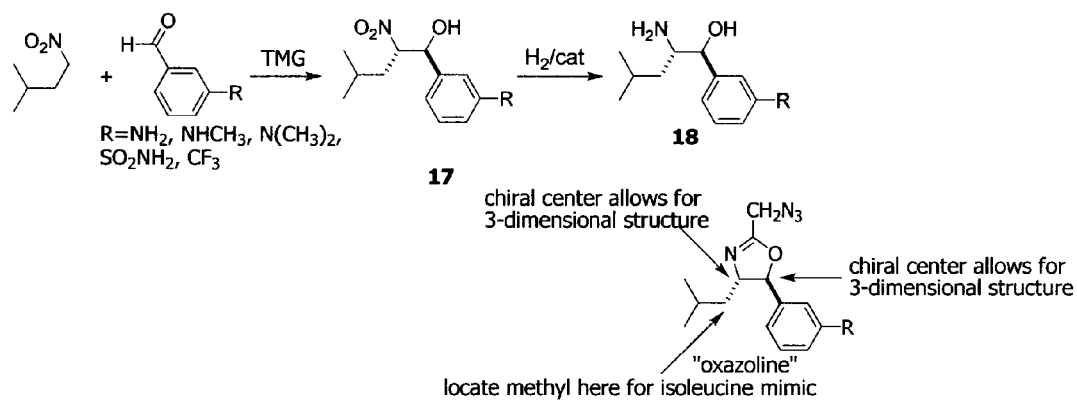
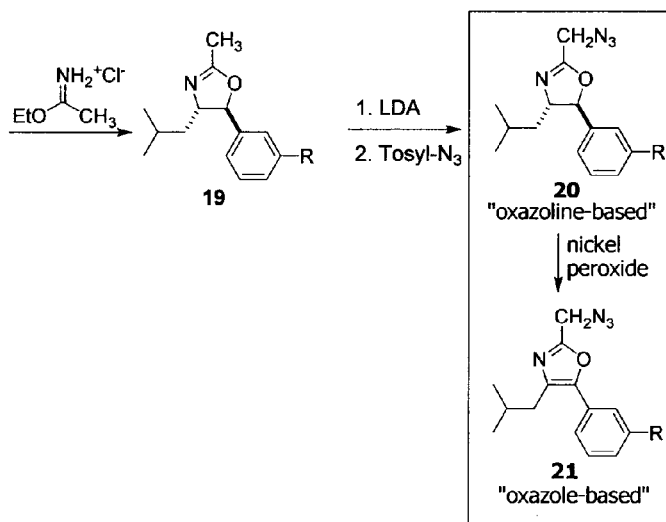
Scheme 6. Example of "click" chemical reaction between Group I VXXLL BAR Inhibitor and Oxazole-Based NITVK Inhibitor
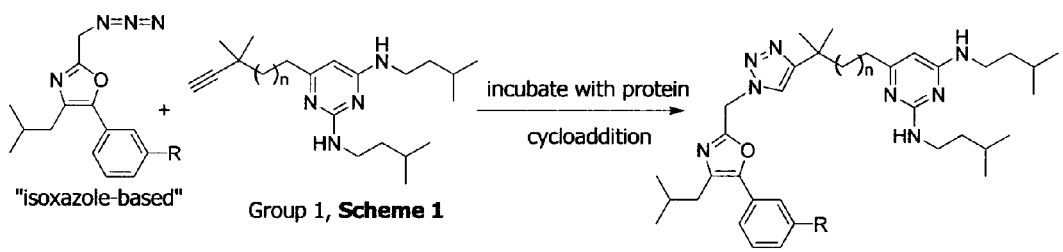

Figure 7

Examples of Variation in Oxazole Scaffold Structure:

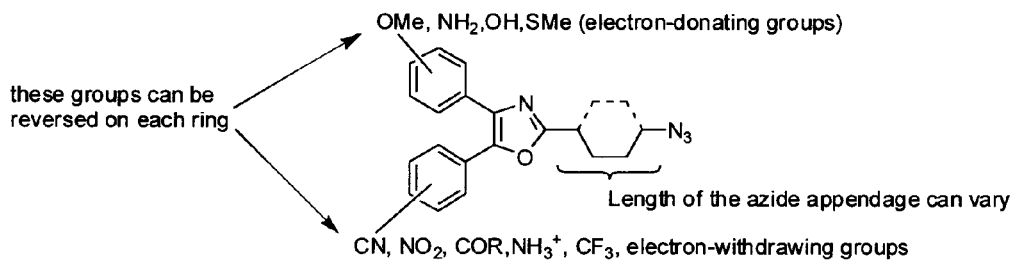

Basic Scaffold Substitution

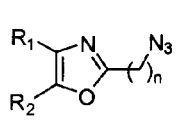

$R_1$=Aryl(e.g. substituted phenyl) or lipophilic hydrocarbon group $R_2$=Aryl(e.g. subustituted phenyl) or lipophilic hydrocarbon group (The positions of $R_1, R_2$ on the oxazole ring may be reversed)

Synthesis of azidoalkyl "click" oxazoles

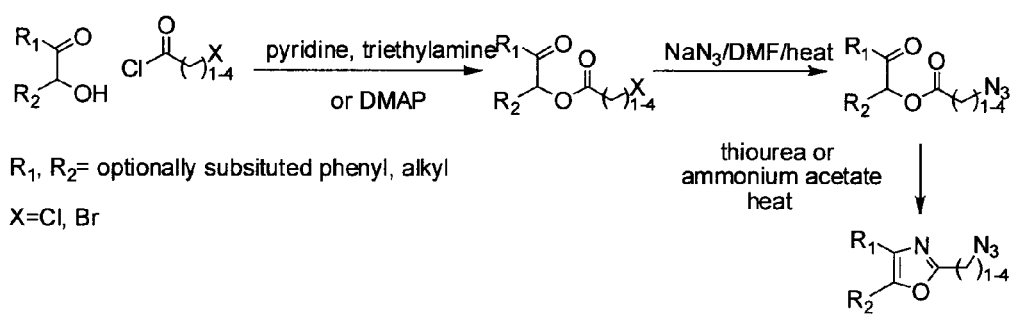

$R_1$, $R_2$= optionally subsituted phenyl, alkyl

X=Cl, Br

Synthesis of azidoaryl "click" oxazoles
(thiourea cyclization method is not compatible with the arylazide group)

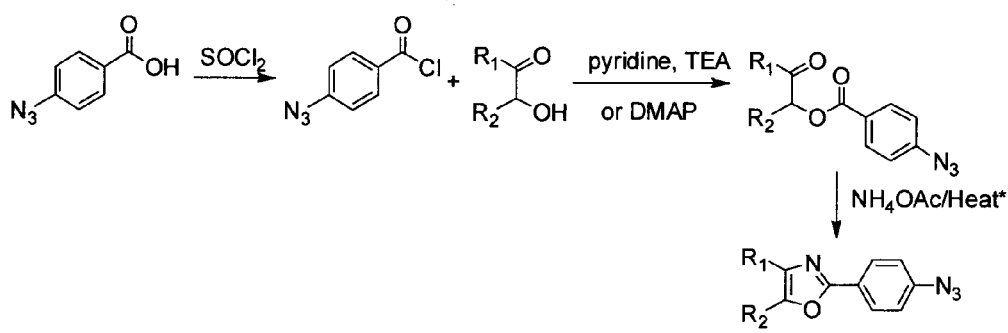

For both the above schemes, it is possible to have $R_1$=ortho, meta, para or $R_2$=ortho, meta, para substituents on both rings or alternating substitutents which are either electron withdrawing groups (EWG) or electron donating groups (EDG). It is also possible to have multiple groups on each ring.

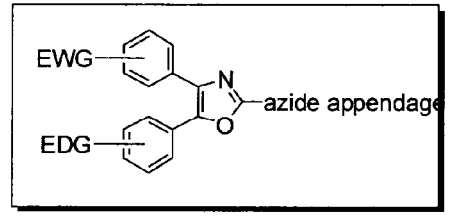

Synthesis of acetylenic Coupling Partners:

TBAF=tetra-*n*-butylammonium fluoride

ANTI-BIOFILM COMPOUNDS

CROSS REFERENCE TO RELATED APPLICATION

This is a National State application under 35 U.S.C. §371 of International Application No. PCT/US2012/047635, filed Jul. 20, 2012, which claims the benefit of priority of U.S. application Ser. No. 61/510,907 filed Jul. 22, 2011, which applications are hereby incorporated by reference.

FEDERAL GRANT SUPPORT

This invention was made with government support under RO1DE023206 awarded by the National Institutes of Health. The government has certain rights in the invention.

BACKGROUND OF THE INVENTION

Adult periodontitis is associated with elevated levels of several Gram negative organisms in the subgingival oral biofilm, including the asaccharolytic, obligate anaerobe *Porphyromonas gingivalis*. In this primary niche, *P. gingivalis* interacts with a variety of other Gram negative obligate and facultative anaerobes, such as *Fusobacterium nucleatum, Treponema denticola*, and *Tannerella forsythus* through specific receptor-ligand interactions. However, the initial colonization of the oral cavity by *P. gingivalis* likely occurs through adherence to organisms in the supragingival biofilm and the successful colonization of this niche by *P. gingivalis* is contingent upon a variety of factors such as reduced oxygen tension and sufficient nutritional sources. Consistent with this, *P. gingivalis* has been shown to also adhere to organisms in supragingival plaque that may provide it with physiologic support, such as *Streptococcus gordonii* and *F. nucleatum*.

SUMMARY OF THE INVENTION

The present invention provides therapies to treat or prevent the onset of periodontal disease, one of the most common bacterial infections of humans (~35% of the adult population worldwide exhibits symptoms of periodontal disease). Because the target for the inhibiting compound is the adherence of *P. gingivalis* to supragingival plaque, it is effective in mouth rinses and toothpaste formulations. Such formulations are easily and non-invasively administered by dental practitioners during routine office visits, or are developed into consumer products for home use. *P. gingivalis* gains systemic exposure through damage to gingival tissues. Therefore, limiting the *P. gingivalis* adherence to supragingival plaque in the oral cavity has a dramatic effect on systemic diseases that are associated with the organism, such as atherosclerosis and heart disease.

Current treatment for periodontitis involves removal of all bacteria from the subgingival pockets. Removal of subgingival plaque by current treatment methods is temporary, since the subgingival packet may be re-colonized after cleaning by organisms from the supragingival reservoir. The present technology is specific for the pathogenic organism and will likely not influence the benign or helpful organisms that inhabit the oral cavity. There are currently no pathogen specific treatments available for oral diseases such as periodontal disease. The present inhibiting compound provides long term control of *P. gingivalis* populations in the oral cavity because it prevents the initial formation of *P. gingivalis* biofilms, as well as disrupting pre-existing biofilms. It is formulated in a way to allow daily exposure allowing it to target organisms in the reservoir in supragingival plaque.

The present invention provides a compound of formula I:

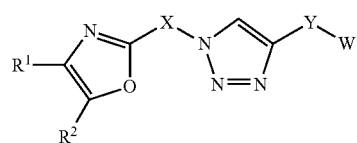

wherein:
X is —(C$_1$-C$_8$)alkyl-, aryl or -aryl(C$_1$-C$_8$)alkyl-;
Y is —(C$_1$-C$_8$)alkyl- or absent;
W is heteroaryl, (C$_3$-C$_7$)carbocycle or aryl, wherein any heteroaryl, (C$_3$-C$_7$)carbocycle or aryl of W is optionally substituted with one or more (e.g. 1, 2, 3, 4 or 5) Z$^1$ groups;
R$^1$ is (C$_1$-C$_8$)alkyl, (C$_2$-C$_8$)alkenyl, (C$_2$-C$_8$)alkynyl or aryl, wherein aryl is optionally substituted with one or more (e.g. 1, 2, 3, 4 or 5) groups selected from (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_a$, —SR$_a$, —S(O)$_2$NR$_b$R$_c$, —NR$_b$R$_c$, —NR$_a$COR$_d$, —C(O)R$_a$, —C(O)OR$_a$ and —C(O)NR$_b$R$_c$;
R$^2$ is (C$_1$-C$_8$)alkyl, (C$_2$-C$_8$)alkenyl, (C$_2$-C$_8$)alkynyl or aryl, wherein aryl is optionally substituted with one or more (e.g. 1, 2, 3, 4 or 5) groups selected from (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_e$, —SR$_e$, —S(O)$_2$NR$_f$R$_g$, —NR$_f$R$_g$, —NR$_e$COR$_h$, —C(O)R$_e$, —C(O)OR$_e$ and —C(O)NR$_f$R$_g$;
each R$_a$ is independently selected from H, (C$_1$-C$_8$)alkyl, (C$_2$-C$_8$)alkenyl, (C$_2$-C$_8$)alkynyl, (C$_3$-C$_7$)carbocycle and aryl;
R$_b$ and R$_c$ are each independently selected from H, (C$_1$-C$_8$)alkyl, (C$_2$-C$_8$)alkenyl, (C$_2$-C$_8$)alkynyl, (C$_3$-C$_7$)carbocycle and aryl, or R$_b$ and R$_c$ together with the nitrogen to which they are attached form a 5, 6 or 7-membered heterocycle;
R$_d$ is independently selected from (C$_1$-C$_8$)alkyl, (C$_2$-C$_8$)alkenyl, (C$_2$-C$_8$)alkynyl, (C$_3$-C$_7$)carbocycle and aryl;
each R$_e$ is independently selected from H, (C$_1$-C$_8$)alkyl, (C$_2$-C$_8$)alkenyl, (C$_2$-C$_8$)alkynyl, (C$_3$-C$_7$)carbocycle and aryl;
R$_f$ and R$_g$ are each independently selected from H, (C$_1$-C$_8$)alkyl, (C$_2$-C$_8$)alkenyl, (C$_2$-C$_8$)alkynyl, (C$_3$-C$_7$)carbocycle and aryl, or R$_f$ and R$_g$ together with the nitrogen to which they are attached form a 5, 6 or 7-membered heterocycle;
R$_h$ is selected from (C$_1$-C$_8$)alkyl, (C$_2$-C$_8$)alkenyl, (C$_2$-C$_8$)alkynyl, (C$_3$-C$_7$)carbocycle and aryl;
each Z$^1$ is independently selected from (C$_1$-C$_8$)alkyl, (C$_2$-C$_8$)alkenyl, (C$_2$-C$_8$)alkynyl, aryl, heteroaryl, —OR$_i$, —NR$_j$R$_k$, and —NR$_i$COR$_m$, wherein any aryl or heteroaryl of Z$^1$ is optionally substituted with one or more (e.g. 1, 2, 3, 4 or 5) (C$_1$-C$_8$)alkyl;
each R$_i$ is selected from H and (C$_1$-C$_8$)alkyl;
R$_j$ and R$_k$ are each independently selected from H and (C$_1$-C$_8$)alkyl;
R$_m$ is (C$_1$-C$_8$)alkyl optionally substituted with one or more (e.g. 1 or 2) —N(R$_n$)$_2$ or —N(R$_n$)$_3$$^+$Q$^-$ wherein Q$^-$ is halogen; and
each R$_n$ is independently H or (C$_1$-C$_8$)alkyl;
or a salt thereof.

The terms "protein," "peptide" and "polypeptide" are used interchangeably herein. Peptide sequences specifically recited herein are written with the amino terminus on the left and the carboxy terminus on the right.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

BRIEF DESCRIPTION OF FIGURES

FIG. 2. Synthesis schemes for Group 1 and Group 2 precursors.

FIG. 4. Amino acid substitutions that promote or reduce *P. gingivalis* adherence to streptococci.

FIG. 5. Synthesis of NITVK (SEQ ID NO:2) mimics (Scheme 5) and illustration of a Mfa-catalyzed click (cycloadditon) reaction to form a potential inhibitor of the Mfa-AgI/II interaction (Scheme 6).

FIG. 7. Examples of variation in oxazole scaffold structures, the synthesis of azidoalkyl "click" oxazoles and the synthesis of azidoaryl "click" oxazoles.

DETAILED DESCRIPTION

Figure 1A:
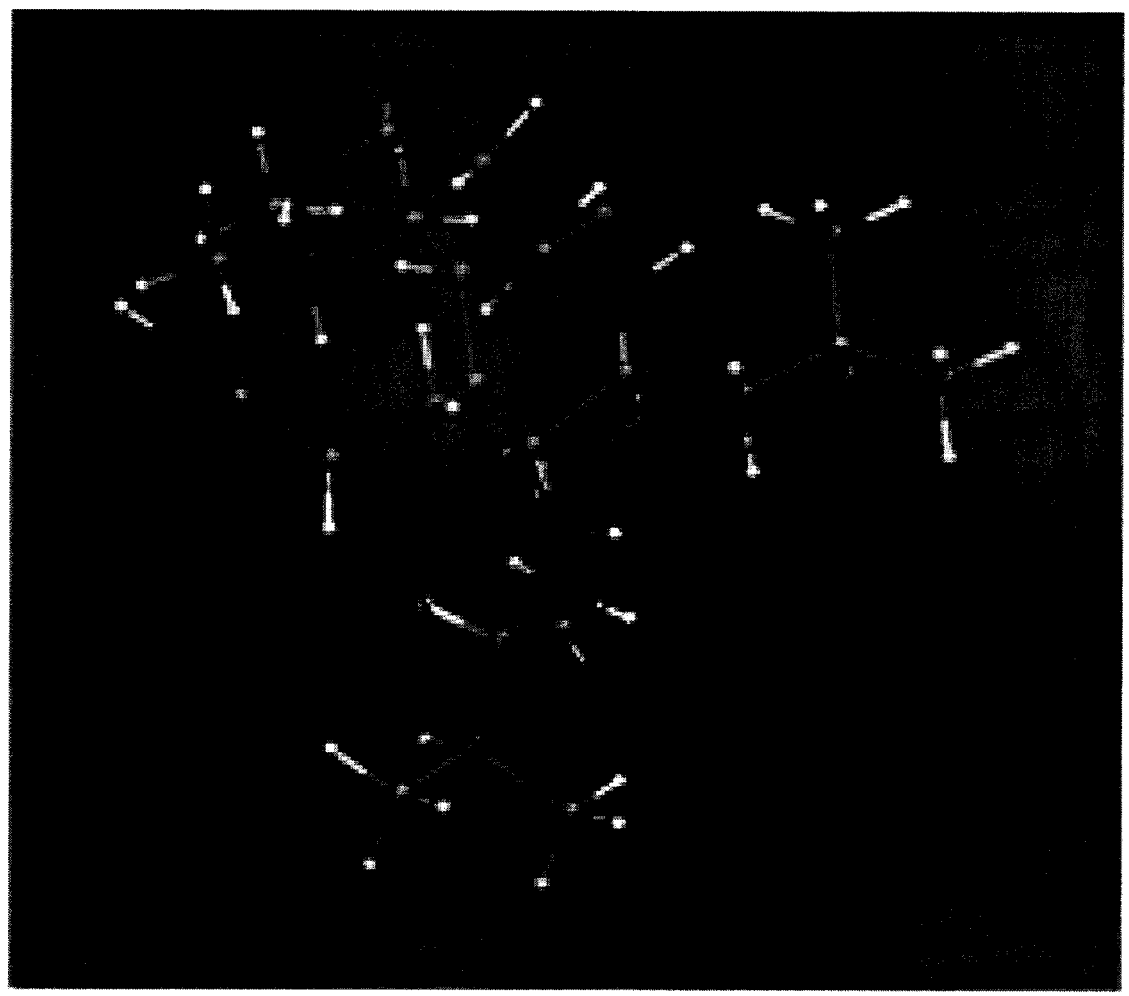
FIGS. 1A and 1B. Molecular modeling of the VXXLL (SEQ ID NO:1) motif illustrate the structural basis for the "outside in" (A) and "inside out" (B) strategies for the design of VXXLL (SEQ ID NO:1) mimics.

*P. gingivalis* is strongly associated with adult periodontitis and is also linked to atherosclerosis, heart disease and preterm births. In the oral cavity, this organism resides in the subgingival pocket and exists in concert with a complex microbial community called a biofilm (dental plaque). However, to reach its primary niche in the subgingival pocket, *P. gingivalis* must first attach to bacterial cells that are present in supragingival dental plaque. *P. gingivalis* colonizes supragingival plaque by adhering to organisms such as *Streptococcus gordonii*. Thus, supragingival plaque may represent a biologic reservoir for *P. gingivalis* in the oral cavity. Because the *P. gingivalis*-*S. gordonii* interaction represents one of the first reactions that allows *P. gingivalis* to colonize the oral cavity, it is a good target for therapeutic intervention of periodontitis and systemic diseases associated with *P. gingivalis*. Controlling and/or preventing this pathogen from occupying its supragingival niche may limit its access to the preferred subgingival niche that is essential for *P. gingivalis* to exert its pathogenic properties.

Adherence of *P. gingivalis* to *S. gordonii* is mediated by a protein-protein interaction between the fimbrial protein Mfa of *P. gingivalis* and the streptococcal antigen I/II polypeptide. The inventors have dissected this interaction and have identified a specific peptide derived from antigen I/II that binds to Mfa and potently inhibits ($I_{50}$=1.3 µM) the development of *P. gingivalis* biofilms on streptococci. Site specific mutagenesis studies identified a structural motif comprised of the amino acids NITVK (SEQ ID NO:2) that was essential for biofilm inhibitory activity of the peptide. This region alone is not sufficient for biofilm inhibition. An second motif is also required, which includes the amino acids VXXLL (SEQ ID NO:1), where X is any amino acid. Either motif alone is inactive for inhibition of *P. gingivalis* biofilm formation.

A "biofilm" is a complex organization of bacteria that are anchored to a surface via a bacterially extruded exopolysaccharide matrix, and grow into differentiated towers that can be several hundred bacteria in height. The extruded exopolysaccharide matrix, which comprises more than 90% of the biofilm, envelopes the bacteria and provides protection from phagocytosis and oxidative burst mechanisms, both in natural environments and in the host. Bacteria within biofilms are also resistant to the host's humoral defense systems because or a lack of accessibility by immunoglobulin and complement. The attachment of bacteria to a surface triggers the expression of a cassette of genes, which results in the formation of a biofilm A "biofilm phenotype" confers to a bacterium with reduced metabolic activity and enhanced antibiotic resistance in comparison with the corresponding planktonic phenotype. A "biofilm-producing bacterium" or "biofilm bacterium" is a bacterium capable of producing, forming, and/or accumulating a biofilm in vitro or in vivo, e.g., on artificial and cellular surfaces.

Compounds of the Present Invention

Unless stated otherwise, the following terms and phrases as used herein are intended to have the following meanings:

"Alkyl" is a straight or branched hydrocarbon. For example, an alkyl group can have 1 to 20 carbon atoms (i.e, ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl) or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —CH($CH_3$)$CH_2CH_3$), 2-methyl-2-propyl and (t-Bu, t-butyl, —$C(CH_3)_3$.

"Alkenyl" is a straight or branched hydrocarbon containing at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$) and 5-hexenyl (—$CH_2CH_2CH_2CH_2$CH=$CH_2$).

"Alkynyl" is a straight or branched hydrocarbon containing at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$)haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1,2,3,4-tetrahydronaphthyl, anthracenyl, and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2, 3 or 4 rings) wherein a heteroaryl group, as defined above, can be condensed with one or more heteroaryls (e.g. naphthyridinyl), heterocycles, (e.g. 1,2,3,4-tetrahydronaphthyridinyl), carbocycles (e.g. 5,6,7,8-tetrahydroquinolyl) or aryls (e.g. indazolyl) to form a multiple condensed ring system. Such multiple condensed ring systems may be optionally substituted with one or more (e.g. 1, 2, 3 or 4) oxo groups on the carbocycle or heterocycle portions of the condensed ring. It is to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g. a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl", "heterocyclic" or "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen).

Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. $(C_3-C_7)$carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4,5]decane, etc), via two adjacent carbon atoms to form a fused connection such as a bicyclo[4,5], [5,5], [5,6] or [6,6] system, or 9 or 10 ring atoms arranged as a bicyclo[5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

It is to be understood that for compounds of the invention when a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diasteromer. In another embodiment, a compound of the invention may be at least 51% a single diasteromer. In another embodiment, a compound of the invention may be at least 60% a single diastereomer. In another embodiment, a compound of the invention may be at least 70% a single diastereomer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

Specific values listed below are values for compounds of formula I.

A specific value for X is phenyl or $(C_1-C_8)$alkyl.

Another specific value for X is —$(C_1-C_8)$alkyl- or aryl.

Another specific value for X is phenyl, methylene, propylene or butylene.

A specific value for W is pyrimidinyl, triazinyl, cyclohexyl or benzoxazolyl, wherein any pyrimidinyl, triazinyl, cyclohexyl or benzoxazolyl of W is optionally substituted with one or more $Z^1$ groups.

A specific value for $Z^1$ is $(C_1-C_8)$alkyl, —NH$(C_1-C_8)$alkyl, —NHCO—$(C_1-C_8)$alkyl-NMe$_3^+$Q$^-$, aryl or heteroaryl, wherein any aryl or heteroaryl of $Z^1$ is optionally substituted with one or more $(C_1-C_8)$alkyl and wherein Q$^-$ is halogen.

Another specific value for $Z^1$ is —NH$(C_1-C_8)$alkyl.

A specific value for W is:

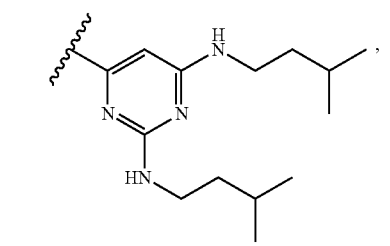

,

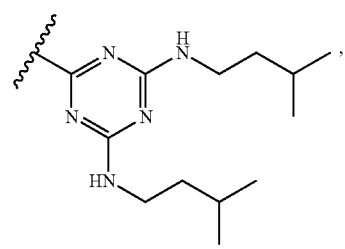

,

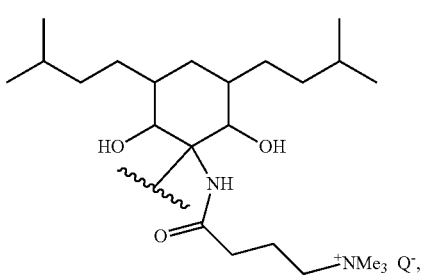

,

Another specific value for W is:

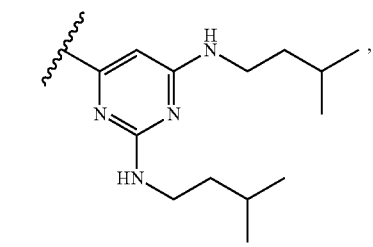

,

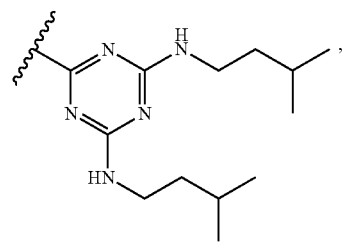

,

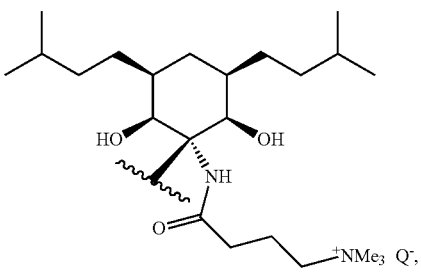

,

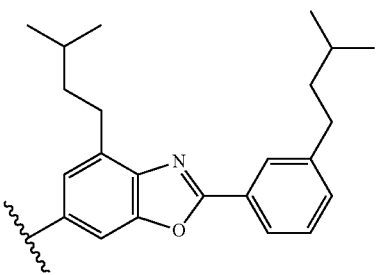

or

9
-continued

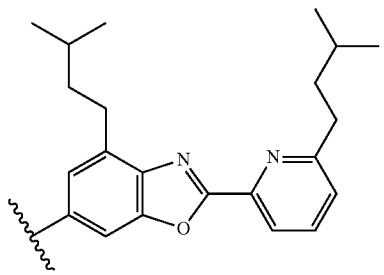

Another specific value for W is:

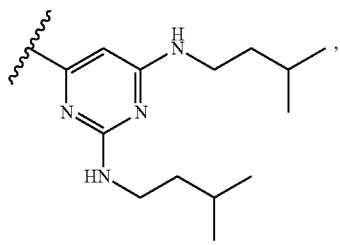

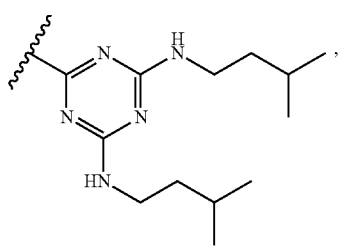

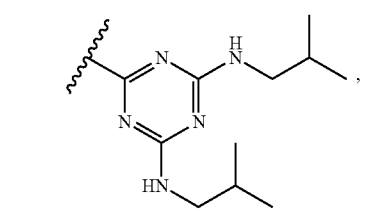

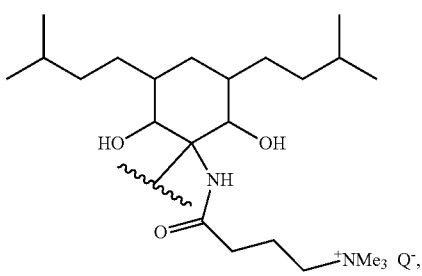

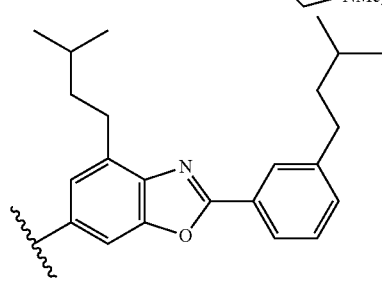

or

10
-continued

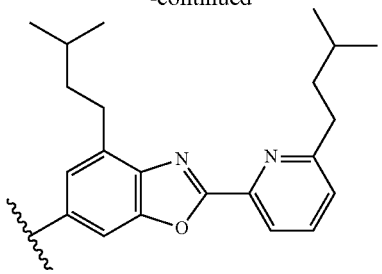

A specific value for $R^1$ is $(C_1-C_8)$alkyl or aryl, wherein aryl is optionally substituted with one or more each groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_a$, —NR$_b$R$_c$, —NR$_a$COR$_d$, —C(O)R$_a$, —C(O)OR$_a$ and —C(O)NR$_b$R$_c$.

Another specific value for $R^1$ is $(C_4-C_6)$alkyl or phenyl, wherein phenyl is optionally substituted with one or more each groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_a$, —NR$_b$R$_c$, —NR$_a$COR$_d$, —C(O)R$_a$, —C(O)OR$_a$ and —C(O)NR$_b$R$_c$.

Another specific value for $R^1$ is phenyl or isobutyl.

A specific value for $R^2$ is $(C_1-C_8)$alkyl or aryl, wherein aryl is optionally substituted with one or more each groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_e$, —NR$_f$R$_g$, —NR$_e$COR$_h$, —C(O)R$_e$, —C(O)OR$_e$ and —C(O)NR$_f$R$_g$.

Another specific value for $R^2$ is $(C_4-C_6)$alkyl or phenyl, wherein phenyl is optionally substituted with one or more each groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_e$, —NR$_f$R$_g$, —NR$_e$COR$_h$, —C(O)R$_e$, —C(O)OR$_e$ and —C(O)NR$_f$R$_g$.

Another specific value for $R^2$ is phenyl, wherein phenyl is optionally substituted with one or more each groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_e$, —NR$_f$R$_g$, —NR$_e$COR$_h$, —C(O)R$_e$, —C(O)OR$_e$ and —C(O)NR$_f$R$_g$.

A specific value for Y is absent.

A specific value for $R_n$ is $(C_1-C_8)$alkyl.

In one embodiment a compound of formula I is selected from:

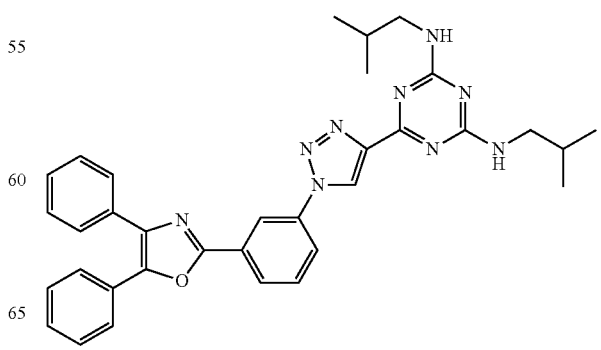

,

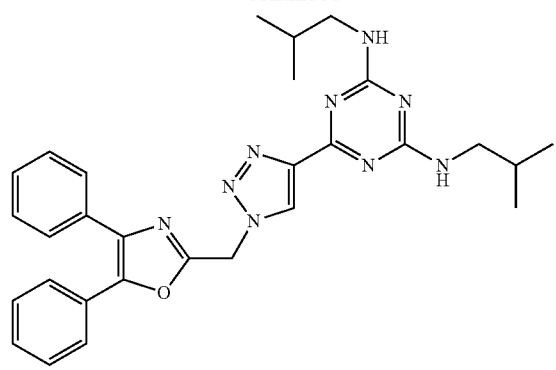

,

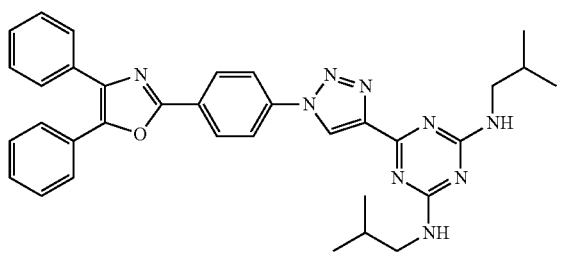

,

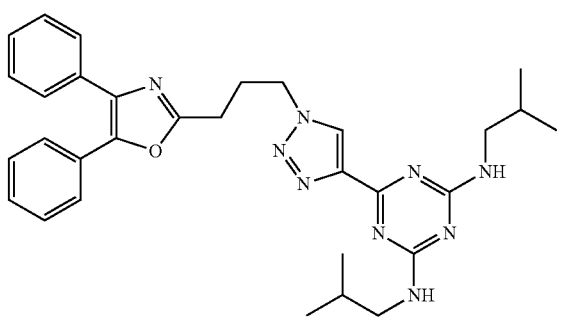

,

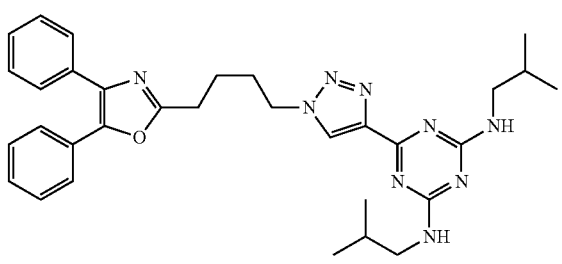

,

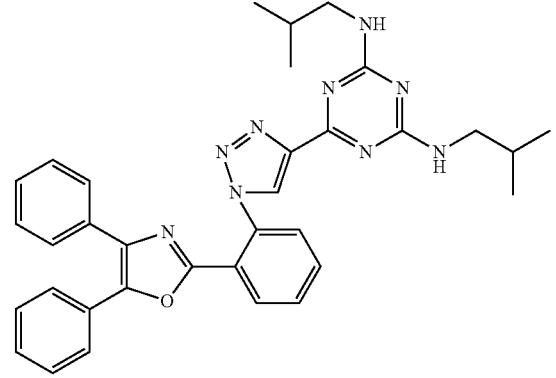

,

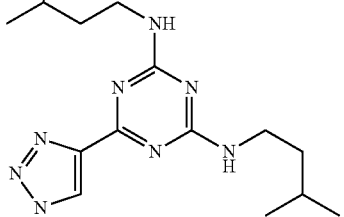

,

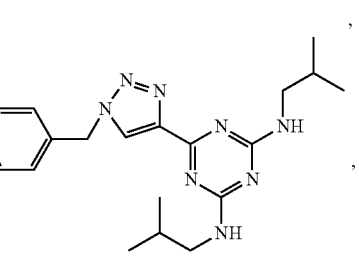

,

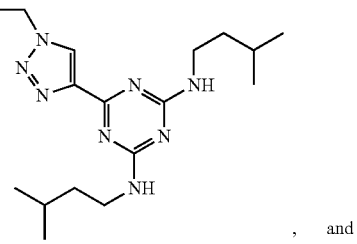

,

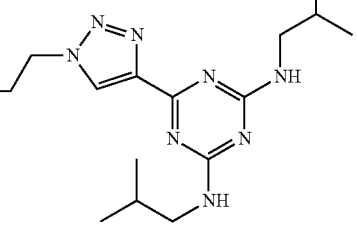

, and

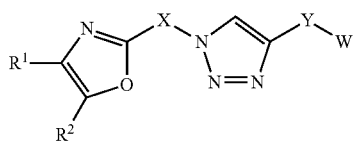

and salts thereof.

In one embodiment the invention provides a compound of formula I:

$$\text{R}^1 \text{ — oxazole — X — triazole — Y — W} \quad \text{I}$$

wherein:
X is $(C_1-C_8)$alkyl or aryl;
Y is $(C_1-C_8)$alkyl;
W is heteroaryl, $(C_3-C_7)$carbocycle or aryl, wherein any heteroaryl, $(C_3-C_7)$carbocycle or aryl of W is optionally substituted with one or more (e.g. 1, 2, 3, 4 or 5) $Z^1$ groups;
$R^1$ is $(C_1-C_8)$alkyl, $(C_2-C_8)$alkenyl, $(C_2-C_8)$alkynyl or aryl, wherein aryl is optionally substituted with one or more (e.g. 1, 2, 3, 4 or 5) groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_a$, —NR$_b$R$_c$, —NR$_a$COR$_d$, —C(O)R$_a$, —C(O)OR$_a$ and —C(O)NR$_b$R$_c$;

R$^2$ is $(C_1-C_8)$alkyl, $(C_2-C_8)$alkenyl, $(C_2-C_8)$alkynyl or aryl, wherein aryl is optionally substituted with one or more (e.g. 1, 2, 3, 4 or 5) groups selected from $(C_1-C_8)$alkyl, $(C_2-C_8)$alkenyl, $(C_2-C_8)$alkynyl, $(C_3-C_7)$carbocycle, halo$(C_1-C_3)$alkyl, —CN, NO$_2$, halogen, —OR$_e$, —NR$_f$R$_g$, —NR$_e$COR$_h$, —C(O)R$_e$, —C(O)OR$_e$ and —C(O)NR$_f$R$_g$;

each R$_a$ is independently selected from H, $(C_1-C_8)$alkyl, $(C_2-C_8)$alkenyl, $(C_2-C_8)$alkynyl, $(C_3-C_7)$carbocycle and aryl;

R$_b$ and R$_c$ are each independently selected from H, $(C_1-C_8)$alkyl, $(C_2-C_8)$alkenyl, $(C_2-C_8)$alkynyl, $(C_3-C_7)$carbocycle and aryl, or R$_b$ and R$_c$ together with the nitrogen to which they are attached form a 5, 6 or 7-membered heterocycle;

R$_d$ is independently selected from $(C_1-C_8)$alkyl, $(C_2-C_8)$alkenyl, $(C_2-C_8)$alkynyl, $(C_3-C_7)$carbocycle and aryl;

each R$_e$ is independently selected from H, $(C_1-C_8)$alkyl, $(C_2-C_8)$alkenyl, $(C_2-C_8)$alkynyl, $(C_3-C_7)$carbocycle and aryl;

R$_f$ and R$_g$ are each independently selected from H, $(C_1-C_8)$alkyl, $(C_2-C_8)$alkenyl, $(C_2-C_8)$alkynyl, $(C_3-C_7)$carbocycle and aryl, or R$_f$ and R$_g$ together with the nitrogen to which they are attached form a 5, 6 or 7-membered heterocycle;

R$_h$ is selected from $(C_1-C_8)$alkyl, $(C_2-C_8)$alkenyl, $(C_2-C_8)$alkynyl, $(C_3-C_7)$carbocycle and aryl;

each Z$^1$ is independently selected from $(C_1-C_8)$alkyl, $(C_2-C_8)$alkenyl, $(C_2-C_8)$alkynyl, aryl, heteroaryl, —OR$_i$, —NR$_j$R$_k$, and —NR$_i$COR$_m$, wherein any aryl or heteroaryl of Z$^1$ is optionally substituted with one or more (e.g. 1, 2, 3, 4 or 5) $(C_1-C_8)$alkyl;

each R$_i$ is selected from H and $(C_1-C_8)$alkyl;

R$_j$ and R$_k$ are each independently selected from H and $(C_1-C_8)$alkyl;

R$_m$ is $(C_1-C_8)$alkyl optionally substituted with one or more (e.g. 1 or 2) —N(R$_n$)$_2$ or —N(R$_n$)$_3^+$Q$^-$ wherein Q$^-$ is halogen; and each R$_n$ is independently $(C_1-C_8)$alkyl;

or a salt thereof.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

In one embodiment of the invention a salt is a pharmaceutically acceptable salt.

Compositions and Methods of Use

The present invention provides a composition including the compound of formula I and a physiologically acceptable carrier. In certain embodiments, the carrier is a mouth rinse, toothpaste, dental floss or chewing gum. In certain embodiments, the carrier is a polymer.

The present invention provides a therapeutic method for preventing or treating a pathological condition or symptom in a mammal, such as a human, wherein an antibiotic activity is implicated and antagonism of its action is desired, by administering to a mammal in need of such therapy, an effective amount of a compound of formula I.

The present invention provides a therapeutic method for preventing or treating a pathological condition or symptom in a mammal, such as a human, wherein anti-biofilm formation activity is implicated and antagonism of its action is desired, comprising administering to a mammal in need of such therapy, an effective amount of a compound of formula I.

The present invention provides a method to treat a microbial infection comprising administering a therapeutically effective amount of a compound of formula I to a mammal. In certain embodiments, the bacteria are gram-negative bacteria, such as, for example, *Porphyromonas gingivalis*.

The present invention provides a compound of formula I for use in medical therapy.

The present invention provides the use of a compound of formula I for the manufacture of a medicament useful for the treatment of a microbial infection in a mammal.

The present invention provides a method of preventing the adhesion of bacteria on a solid substrate comprising contacting the solid substrate with a compound of formula I. In certain embodiments, the compound is dispersed in a polymer.

The present invention provides a method of preventing the formation of a biofilm of bacteria on a solid substrate comprising contacting the solid substrate with a compound of formula I.

The present invention provides a method of preventing the formation of a biofilm of bacteria in vivo comprising contacting a tissue surface with a compound of formula I. In certain embodiments, the tissue is oral or lung tissue. In certain embodiments, the tissue is a mucosal surface. In certain embodiments, the bacteria are gram-negative bacteria, such as, for example, *Porphyromonas gingivalis*.

The compounds of the present invention can be formulated as consumer product compositions and administered to a mammalian host, such as a human in a variety of forms adapted to the chosen route of administration, e.g., orally. In certain embodiments the compound is included in a toothpaste, a mouth rinse or as a coating on a dental floss.

Further, the compounds of the present invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The present invention provides a therapeutic method for preventing or treating a pathological condition or symptom in a mammal (e.g. a human) in need of such therapy, wherein an antibiotic activity is desired, comprising administering to the mammal an effective amount of a compound a compound of formula I or a pharmaceutically acceptable salt thereof.

The present invention provides a therapeutic method for preventing or treating a pathological condition or symptom in a mammal (e.g. a human) in need of such therapy, wherein anti-biofilm formation is desired, comprising administering to the mammal an effective amount of a compound of formula I or a pharmaceutically acceptable salt thereof.

The present invention provides a method to treat a microbial infection in a mammal (e.g. a human) comprising administering a therapeutically effective amount of a compound of formula I or a pharmaceutically acceptable salt thereof to the mammal.

The present invention provides a compound of formula I as described in any one of claims or a pharmaceutically acceptable salt thereof.

The present invention provides the use of a compound of formula I or a pharmaceutically acceptable salt thereof for the manufacture of a medicament for the treatment of a microbial infection in a mammal.

The present invention provides a method of preventing the adhesion of bacteria on a solid substrate comprising contacting the solid substrate with a compound of formula I or a salt thereof.

The present invention provides a method of preventing the formation of a biofilm of bacteria on a solid substrate comprising contacting the solid substrate with a compound of formula I or a salt thereof.

The present invention provides a method of preventing the formation of a biofilm of bacteria in vivo comprising contacting a tissue surface with a compound of formula I or a pharmaceutically acceptable salt thereof.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Compounds of the invention can also be administered in combination with other therapeutic agents, for example, other agents that are useful as antibiotics. Examples of such agents include a protein synthesis inhibitor, a cell wall growth inhibitor, a cell membrane synthesis inhibitor, a nucleic acid synthesis inhibitor, or a competitive enzyme inhibitor. In certain embodiments, the additional agent is an antibiotic such as penicillin, ampicillin, amoxicillin, vancomycin, cycloserine, bacitracin, cephalolsporin, imipenem, colistin, methicillin, streptomycin, kanamycin, tobramycin, gentamicin, tetracycline, chlortetracycline, doxycycline, chloramphenicol, lincomycin, clindamycin, erythromycin, oleandomycin, polymyxin nalidixic acid, rifamycin, rifampicin, gantrisin, trimethoprim, isoniazid, paraminosalicylic acid, or ethambutol.

In certain embodiments, the compound of the invention is contacted with a microbe.

Accordingly, in one embodiment the invention also provides a composition comprising a compound of the present invention, at least one other therapeutic agent, and a pharmaceutically acceptable diluent or carrier. The invention also provides a kit comprising a compound of the present invention, at least one other therapeutic agent, packaging material, and instructions for administering the compound of the present invention or the pharmaceutically acceptable salt thereof and the other therapeutic agent or agents to an animal to prevent bacterial infection.

The present invention also provides a solution that includes a solvent, a polymer dissolved in the solvent and a compound of formula I dispersed in the solvent.

Solid Substrates

In one embodiment of the invention, a solution which includes a solvent, a polymer dissolved in the solvent and a compound of formula I dispersed in the solvent is applied to a solid substrate and then the solvent is evaporated. The inclusion of a polymer in intimate contact with a compound of formula I on the underlying solid substrate allows the compound to be retained on the solid substrate in a resilient matrix during expansion of the solid substrate and also slows the administration of drug following implantation. The method can be applied whether the solid substrate has a metallic or polymeric surface. The method is also an extremely simple method since it can be applied by simply immersing the solid substrate into the solution or by spraying the solution onto the solid substrate. The amount of compound to be included on the solid substrate can be readily controlled by applying multiple thin coats of the solution while allowing it to dry between coats. The overall coating should be thin enough so that it will not significantly increase the profile of the solid substrate. It is therefore preferably less than about 0.002 inch thick and most preferably less than 0.001 inch thick. The adhesion of the coating and the rate at which the compound of formula I is delivered can be controlled by the selection of an appropriate bioabsorbable or biostable polymer and by the ratio of the compound if formula I to polymer in the solution. By this method, the compound can be applied to a solid substrate, be retained on a solid substrate during expansion of the solid substrate, and elute the compound at a controlled rate. The release rate can be further controlled by varying the ratio of compound to polymer in the multiple layers. The release rate can be further controlled by varying the ratio of compound to polymer in the multiple layers. For example, a higher compound-to-polymer ratio in the outer layers than in the inner layers would result in a higher early dose which would decrease over time. Examples of some suitable combinations of polymers and solvent are set forth in Table 1 below.

TABLE 1

| Polymer | Solvent |
| --- | --- |
| poly(L-lactic acid) | chloroform |
| poly(lactic acid-co-glycolic acid) | acetone |
| polyether | N-methyl |
| urethane | pyrrolidone |
| silicone adhesive | xylene |
| poly(hydroxy-butyrate-co-hydroxyvalerate) | dichloro-methane |

The present invention further provides a coated device that includes (a) a solid substrate; and (b) a solid composite of a compound of Formula I and a therapeutic substance in an adherent layer on the solid substrate. In certain embodiments, the solid substrate has a metal surface, or a polymeric surface. In certain embodiments, the solid composite includes a plurality of layers. In certain embodiments, the ratio of therapeutic substance to polymer is varied in some of the layers. In certain embodiments, the polymer is a bioabsorbable polymer. In certain embodiments, the polymer is poly(L-lactic acid), poly(lactide-co-glycolide) or poly(hydroxybutyrate-co-valerate). In certain embodiments, the polymer is a biostable polymer. In certain embodiments, the polymer is a silicone, polyurethane, polyester, vinyl homopolymer or copolymer, acrylate homopolymer or copolymer, polyether or cellulosic, or a combination thereof. In certain embodiments, the ratio of compound to polymer in the layer is in the range of about 10:1 to 1:100.

Examples of various polymers used in forming the agent-eluting component include poly(methyl(meth)acrylate ("PMMA"), ethylenevinylalcohol ("EVAL"), poly(butyl (meth)acrylate) ("PBMA"), biodegradable polymers (i.e., Poly(glycolic acid) ("PGA") and poly(L-lactic acid) ("PLLA"), polyethylene glycol ("PEG"), hyaluronic acid ("HA"), polyester amide ("PEA"), poly(glycerol-sebacate) ("PGS"), nanoscale structures of carbon, acetal copolymer, acetal homopolymer, acrylonitrile butadiene styrene, ABS and polycarbonate, nylon, polyamide, polyacrylate, polyaryl sulfone, polycarbonate, polyetherketone, polyetherimide, polyether sulfone, polyethylene terephthalate, polyimide, polyphenylene oxide, polyphenylene sulfide, polypropylene, polysulfone, polyurethane, polyvinyl chloride, styrene acrylonitrile and other suitable polymers. It is contemplated that the above polymers can be slowly dissolved or chemically degraded or both. As set forth above, the local drug-eluting component alternatively may be fabricated from porous ceramic or various metals or alloys, including stainless steel, platinum, titanium, tantalum, nickel-titanium, cobalt-chromium, and alloys thereof. This family of polymers comprises the following basic components: (1) moieties derived from aliphatic diols, triols, or polyols; (2) moieties derived from polycarboxylic acids (carboxylic acids containing more than one acid functionality); and (3) biobeneficial, non-fouling, or bioactive moieties (U.S. Pat. No. 7,186,789, incorporated by reference herein).

Methods of Manufacture

The present invention provides a method for manufacturing a coated solid substrate by applying to the solid substrate a layer which is a solid composite of polymer and a compound of formula I, wherein the first layer is applied by the steps of: (a) applying to the solid substrate a solution which includes a solvent, a polymer dissolved in the solvent and a compound of formula I dispersed in the solvent; and (b) evaporating the solvent to form a composite of polymer and the inhibitory compound. In certain embodiments, the solution is applied by spraying. In certain embodiments, the solution is applied in a plurality of application and drying steps. In certain embodiments, the ratio of inhibitory compound to dissolved polymer in the solution is varied in some of the plurality of application steps. In certain embodiments, the polymer is a bioabsorbable polymer. In certain embodiments, the polymer is poly(L-lactic acid), poly(lactide-co-glycolide) or poly(hydroxybutyrate-co-valerate). In certain embodiments, the polymer is a biostable polymer. In certain embodiments, the polymer is a silicone, polyurethane, polyester, vinyl homopolymer or copolymer, acrylate homopolymer or copolymer, polyether or cellulosic, or a combination thereof. A typical ratio of compound to dissolved polymer in the solution can vary widely (e.g., in the range of about 10:1 to 1:100).

The invention will now be illustrated by the following non-limiting Examples.

EXAMPLE 1

Design and Synthesis of Anti-biofilm Peptidomimetic Compounds

Caries and periodontitis are likely the most prevalent and costly microbial diseases in humans and are caused by complex multi-species biofilms. In the last several decades, the composition of these biofilms, the pathogenic organisms associated with disease, and how these communities develop and initiate the disease processes have been extensively studied. As a result, understanding of these microbial infections at the molecular and mechanistic levels has dramatically progressed. Yet both caries and periodontitis are still highly prevalent and the treatment and prevention approaches that currently exist consist primarily of removing the entire microbial biofilm rather than targeting specific pathogens without affecting the commensal organisms or other species that may be beneficial to health.

The present example uses the mechanistic and molecular information derived from the inventors' studies of the microbial processes that contribute to periodontitis to design and develop inexpensive therapeutics that specifically target the major periodontal pathogen *Porphyromonas gingivalis*. The basic discoveries that provide the foundation for this invention come from the inventors' molecular characterization of the interspecies association of *P. gingivalis* with commensal oral streptococci, a process which promotes the initial colonization of the oral cavity by the pathogen. From these studies, a peptide that potently inhibits *P. gingivalis* adherence to streptococci both in vitro and in vivo has been developed (WO 2009/108716). The inventors carried out a structure-based approach to design and synthesize peptidomimetics that can be formulated in a mouth rinse or toothpaste that can be made widely available. Given the widespread incidence of periodontitis in the adult population worldwide and the association of *P. gingivalis* with other systemic illnesses such as atherosclerosis and rheumatoid arthritis, a simple and effective therapy that specifically prevents *P. gingivalis* from becoming established in the oral cavity may have a significant impact on the cost of oral health care and the health status of the adult population.

Periodontal disease is prevalent in the adult population worldwide and severe disease, defined as having subgingival pocket depths of greater than or equal to 6 mm, occurs in 5 to 20% of adults. Inclusion of individuals with milder forms of the disease (i.e., pocket depth of 4 to 5 mm) increased the prevalence to 35 to 50% of the adult population. In the US alone, annual expenditures for treatment and prevention of periodontal disease were over 14 billion dollars in 1999. Furthermore, periodontal pathogens have been linked to other systemic diseases such as atherosclerosis, rheumatoid arthritis and pre-term births. Although a causative or mechanistic link between periodontitis and these systemic diseases has not yet been firmly established, it is clear that by controlling periodontal disease the health status of the adult population worldwide can be significantly improved.

Adult periodontitis is strongly associated with a consortium of anaerobic bacteria designated as the "red complex," comprising *P. gingivalis, Tannerella forsythsis* and *Treponema denticola*. Current methods to treat or prevent periodontitis involve removal of the entire microbial biofilm from the subgingival pocket and surgery, if necessary to reduce pocket depth. In general, treatments that prevent or limit re-colonization of the oral cavity by pathogens after treatment, or therapies that specifically target periodontal pathogens like *P. gingivalis* are lacking. However, the potential significance and impact on oral health status of controlling or reducing periodontal disease in the adult population is high. Thus, alternative therapeutic approaches to control or prevent periodontal disease need to be developed. The inventors' basic discoveries that define mechanisms of colonization of the oral cavity by *P. gingivalis* put them in a unique position to design and develop new pathogen-specific therapeutics. The current invention resulted in novel targeted therapeutic agents that inhibit an initial interspecies interaction that facilitates *P. gingivalis* colonization of the oral cavity. These compounds limit *P. gingivalis* populations in the oral cavity by preventing the occupation of its initial niche. They are particularly effective in controlling *P. gingivalis* populations by limiting re-colonization of the oral cavity after scaling and root planing. Although the etiology of periodontitis is complex, in vitro biofilm experiments show that *P. gingivalis* and *T. denticola* (another "red group" organism) exhibit synergy and grow in biofilms much better together than individually. Thus, targeting only *P. gingivalis* in this dual species community affects the entire community. Specific organisms in a biofilm are important contributors to the community as a whole and removal of these "keystone" species impacts the overall vitality and virulence potential of the entire consortium.

Although the primary niche of *P. gingivalis* is the subgingival pocket, it must first colonize the supragingival biofilm upon entry into the oral cavity. Previous results suggest that prior to colonizing its subgingival niche, *P. gingivalis* first interacts with organisms such as commensal streptococci. Since these interactions represent some of the first events that allow *P. gingivalis* to become established in the oral cavity, they represent ideal points for therapeutic intervention to control colonization (or re-colonization) of oral tissues. *P. gingivalis* adherence to streptococci is species specific and is driven by a protein-protein interaction that occurs between the minor fimbrial antigen (Mfa) of *P. gingivalis* and the antigen VII (AgI/II) polypeptide of streptococci. This interaction induces a response in *P. gingivalis* that facilitates its adaptation to biofilm growth in the oral cavity. An essential domain in AgI/II resembles the eukaryotic nuclear receptor (NR) box protein-protein interaction domain and it has been shown that variation in the sequence and structure of the NR box in different AgI/II proteins accounts for the selectivity of *P. gingivalis* adherence to streptococci. The NR box is comprised of two functional peptide motifs, VXXLL (SEQ ID NO:1) and NITVK (SEQ ID NO:2), and a synthetic peptide (designated BAR) encompassing both motifs potently inhibits *P. gingivalis* adherence and formation of biofilms on streptococcal substrates. This peptide is also capable of disrupting existing *P. gingivalis* biofilms. *P. gingivalis* colonization of the oral cavity is controlled by preventing its initial association with streptococci and inhibitors of the Mfa-AgI/II interaction represent potential therapeutic agents to control or prevent periodontal disease.

Although a peptide inhibitor has already been developed, peptide-based therapeutics are limited by the high cost of peptide synthesis and their susceptibility to proteases expressed by oral organisms, including *P. gingivalis* itself. The challenge is to design and produce potent, stable non-peptide inhibitors that mimic the natural peptide substrate bound by Mfa. One traditional approach to identify non-peptide based inhibitors of the Mfa-AgI/II interaction is to screen a large compound library to isolate the few functional inhibitors that the initial library may contain. This strategy, however, has limitations since it is both costly and time consuming.

To overcome these limitations, the inventors used the structural and biochemical information of the Mfa-AgI/II interaction derived from their previous work to design and synthesize non-peptide based inhibitors of the Mfa-AgI/II interaction using a novel organic synthetic approach called in situ click chemistry. Click chemistry is a target guided synthesis that has a number of novel and innovative features that make it an ideal approach for synthesis of BAR peptidomimetics. Click chemistry employs the bio-orthogonal [1,3]-dipolar cycloaddition reaction between azides and acetylenes to produce five membered nitrogen heterocyclic products. This reaction is self-contained and requires no additional reactants, catalysts or byproducts. Importantly, although there is a large thermodynamic driving force for the cycloaddition reaction, there is also a high kinetic barrier that must be overcome, which causes the reaction to be slow at room temperature unless the reactive groups are in close proximity or otherwise activated. In situ click chemistry exploits this characteristic of the reaction and uses a biologic scaffold, e.g., a binding site or an enzyme active site, to select for reagents that tightly bind and position the reactants in close proximity to facilitate the cycloaddition reaction under mild reaction conditions. Essentially, the biologic scaffold directs the synthesis of its own inhibitors.

An additional advantage of the click reaction is that the cycloaddition products are generally nontoxic, are very stable to acidic and basic hydrolysis and are stable in severe oxidative and reductive environments. This facilitates the rapid formulation of active compounds and suggests that the compounds will exhibit long term stability in these formulations. The triazole products that are formed are capable of participating in hydrogen bonding, dipole-dipole and/or π interactions. Thus, the click products can, or can be engineered to contribute to the binding to the biologic template through interactions that are not possible with the precursor compounds alone. This allowed the inventors to design and synthesize compounds that bind very tightly to Mfa and are extremely potent inhibitors.

The experiments described below teach the design and synthesis of precursor reagents and the subsequent Mfa-mediated in situ coupling of these building blocks to generate functional inhibitors (click chemistry reaction products). The general strategy was to design reactive precursors containing the appropriate azide or acetylene groups based on the structural and biochemical properties of each of the two functional amino acid motifs, VXXLL (SEQ ID NO:1) and NITVK (SEQ ID NO:2) in the NR box region of AgI/II. The precursors that react in the presence of purified Mfa protein and Mfa-catalyzed products are identified and purified. Bioactivity of the click products is assessed by a variety of in vitro and in vivo approaches already developed by the inventors, including direct protein binding assays, open flow dual species biofilm cultures and in vivo mouse model of periodontitis.

Experimental Design of Precursor Compounds: The interaction of AgI/II with Mfa is driven by a protein-protein interaction domain that resembles the eukaryotic nuclear receptor (NR) box. The sequence of the inhibitory peptide (BAR) derived from AgI/II is the following: LEAAPKK VQDLLKKANITVKGAFQLFS (SEQ ID NO:3). The NR box-like core element VXXLL (SEQ ID NO:1) is underlined. The NITVK (SEQ ID NO:2) motif that dictates the selectivity of *P. gingivalis* adherence is double underlined. Two amino acid motifs in the NR box-like region of AgI/II are essential. The first motif is a core α-helical region with the sequence VQDLL (SEQ ID NO:4). This motif resembles the core consensus sequence of the eukaryotic NR box (LXXLL (SEQ ID NO:5)). The core element forms an amphipathic α-helix that interacts with a hydrophobic groove in the nuclear receptor ligand binding domain via the hydrophobic leucine residues. Experimental evidence with the VXXLL (SEQ ID NO:1) motif indicates that the structural and functional characteristics of the eukaryotic core sequence are conserved in AgI/II. This suggests that hydrophobic interactions primarily drive the association of the VXXLL (SEQ ID NO:1) motif with Mfa. The second motif is NITVK (SEQ ID NO:2), which is discussed in detail below. The basic strategy for synthesizing inhibitors of the Mfa-AgI/II interaction was to generate compounds that mimic each of these motifs and join them via in situ click chemistry using Mfa as the catalyst.

Reactive precursor compounds were designed that entailed direct modeling of the VXXLL (SEQ ID NO:1) and NITVK (SEQ ID NO:2) motifs. The structure of the VQDLL (SEQ ID NO:4) motif was optimized using the Gaussian 2003 Program Suite and visualized using Visual Molecular Dynamics (VMD). A "head-on" view of the of the peptide sequence reveals an arrangement which resembles an equilateral triangle with each corner falling on the central alkane carbons of the two leucine residues and the valine residue (see FIG. 1A). In designing the small molecule mimics for VXXLL (SEQ ID NO:1), several approaches were used. The first approach encompassed an "outside in" arrangement of the targets in which hydrophobic appendages mimicking the valine and leucine residues were attached to a central scaffold that resides out of the hydrophobic pocket. Thus, the central scaffold is the mimic for the helix backbone which is outside of the hydrophobic groove and the hydrophobic residue element proceeds into the deep hydrophobic groove. With the three hydrophobic substituents in place on the central scaffold, all that remains is attachment of the "click" reacting partner appendage, usually a terminal alkyl acetylene or a terminal alkyl azide. These compounds were designated as Group 1.

Figure 1B:
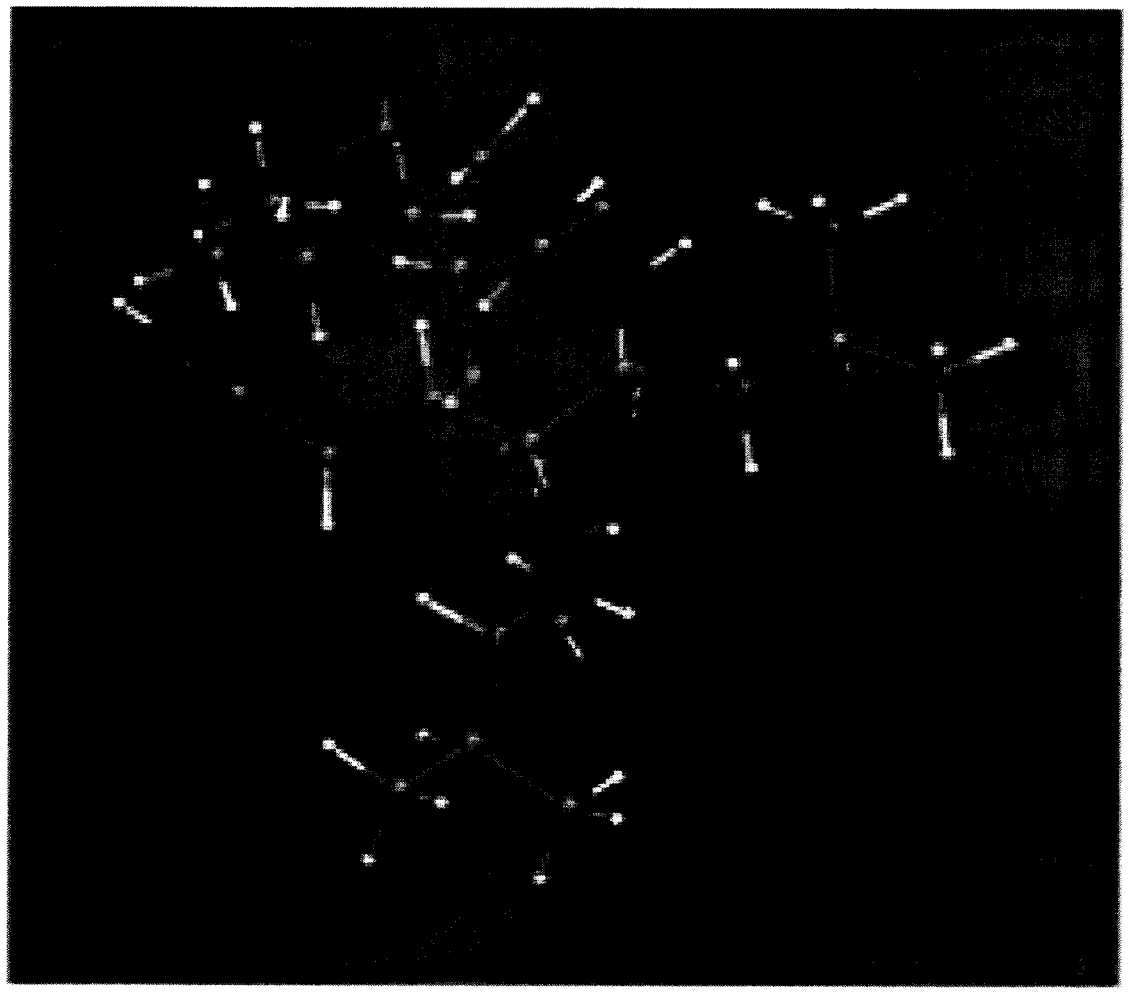

The second approach entailed an "inside out" design (designated as Group 2). When addressing the face of the α-helix of the NR box, the most deeply buried hydrophobic residues fall in almost parallel orientation and may be collectively mimicked by a single molecular fragment as shown in FIG. 1B. The flexible linkers, which incorporate the most hydrophobic part of the leucine residues, extend outward from a semi-rigid molecular scaffold that possesses polar functionalities characteristic of the basic helix. As in the design of the Group 1 compounds, the Group 2 targets will possess the required "click" reacting appendage.

As shown in FIG. 2, the synthesis of the Group 1 compounds utilized a number of basic scaffolds used in pharmacophore design and are amenable to scale-up. The first target of the Group 1 compounds employ a pyrimidine scaffold with two 3-methyl-1-butylamino side chains that will mimic the leucine residues together with a single side chain which will mimic both the valine and bear the acetylenic "click" fragment.

The synthetic sequence starts with the ketoester 1 which can have a variable carbon chain (n=1-3) bearing the terminal acetylene moiety. The length of the acetylenic side chain is easily adjusted for optimum binding and exposure of the terminal triple bond to the azide coupling partner out of the hydrophobic pocket (Scheme 1). The reaction of 1 with thiourea under basic aqueous conditions provides the thiouracil 2. Treatment of the thiouracil 2 with chloroacetic acid followed by chlorination with $POCl_3$ furnishes the dichloropyrimidine 3. Substitution of both chlorines with 3-methyl-2-butylamine affords the target VXXLL (SEQ ID NO:1)-modeled pyrimidine binding inhibitor shown in the shaded box.

A second set of Group 1 inhibitors utilize the symmetrical triazene as the central scaffold with variable-length mimics of the leucine side chains (Scheme 2). The readily-available cyanuric chloride 4 is reacted with a wide range of nucleophiles and organometallic reagents to provide a rich array of targets. Hence, 4 is treated with the acetylenic Grignard reagent 5 thereby providing the acetylenic dichlorotriazene 6. Substitution of the two remaining chlorines of 6 is accomplished with isobutylamine (N=1) or 3-methyl-1-butylamine (N=2) to give the triazene-based inhibitor as shown in the shaded box. Again, the length of the acetylenic side chain is variable so as to optimize the exposure of the acetylene to the click reaction. Similarly, to optimize binding of one of the two or both leucine-mimic residues, in certain embodiments, the amine co-reactants is lengthened to five carbons as exemplified as opposed to the four-carbon amine fragments shown. The common feature of both Group 1 scaffolds is the planarity imparted by the pyrimidine and triazene ring systems. In contrast to the more planar scaffolds in the tri-substituted Group 1 compounds, a more three-dimensional array offered by the cyclohexane ring system is proposed in which more substitutions are available through the tetrahedral nature of the ring carbons.

The symmetrical dialdehyde 7, having the two leucine side chain-mimic residues, is reacted with the nitroacetylene 8 in a "double Henry" reaction, catalyzed by 1,1,3,3-tetramethylguanidine (TMG). The base-catalyzed "double Henry" or, more commonly, the nitroaldol reaction of 7 and 8 afford the symmetrical nitro cyclohexanediol 9 (Luzzio, F. A. 2001. The Henry Reaction: Recent examples. Tetrahedron 57:915-945). Reduction of the nitrodiol 9 to the aminodiol 10 with any number of reducing agents such as hydrogen gas, lithium aluminum hydride or aluminum amalgam followed by N-acylation with 4-N-phthaloylbuytryl chloride will afford the symmetrical amide 11. Deprotection of the 4-N-phthaloyl group with hydrazine followed by exhaustive alkylation with iodomethane will give the Group 1 cyclohexandiol scaffold target with both the "charge clamp" and acetylene click linker moieties as shown in the shaded box (Scheme 3). We anticipate that during the double Henry reaction, catalyzed by a strong base 1,1,3,3-tetramethylguanidine, the acetylenic side chain and the two methylbutyl side chains will assume the more stable cis, cis-diequatorial conformation through equilibration of the dialdehyde as depicted in the scheme.

Figure 3:
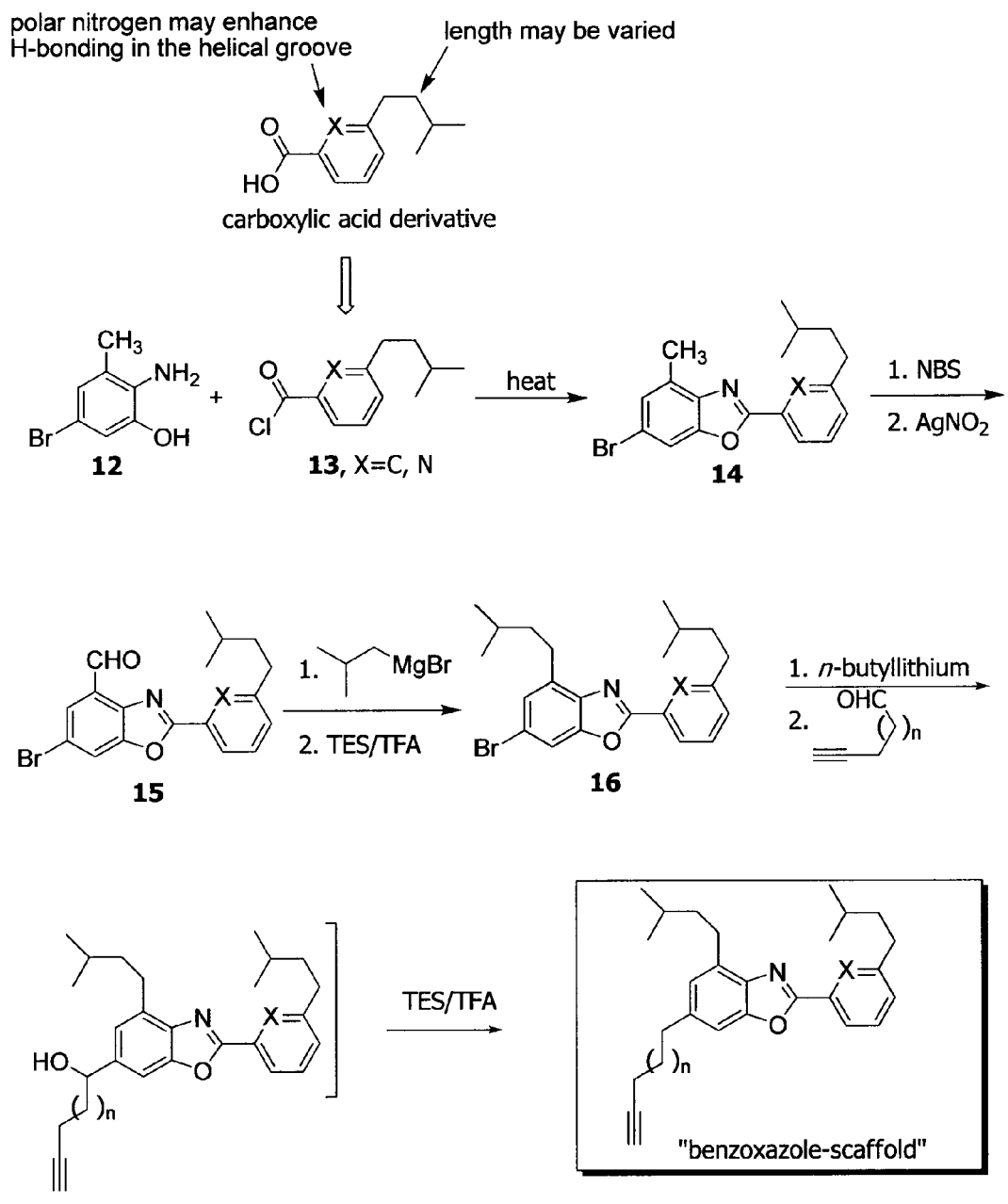
FIG. 3. Synthesis schemes for Group 2 compounds.

As shown in FIG. 3, the Group 2 scaffold targets make use of the well-known benzoxazole heterocyclic core and will allow for the deep reach of the hydrophobic leucine side chain mimics (Scheme 4). 2-Amino-4-bromocresol 12 will be reacted with acid chloride 13 (X=C or N) thereby forming the benzoxazole 14 through acylation/dehydration. Alternatively, in other embodiments, the corresponding carboxylic acid from which 13 is derived is reacted with nitrophenol 12 in the presence of dicyclohexylcarbodiimide to furnish 14. The next sequence of reactions was developed in an earlier pharmacophore synthesis utilizing functionalized benzoxazoles (Luzzio, F. A.; Wlodarczyk, M. T. 2009. Preparation of Benzoheterocyclic Carbaldehydes. Tetrahedron Lett. 50:580-583). Benzoxazole 14 is subjected to free-radical dibromination (N-bromosuccinimide/azobisisobutylnitrile) followed by hydrolysis with silver nitrite/DMSO thereby providing the benzoxazole aldehyde 15. Exposure of the aldehyde 15 to isobutylmagnesium bromide followed by deoxygenation of the intermediate secondary alcohol with triethylsilane/trifluoroacetic acid furnishes the bromobenzoxazole 16 with both side chains installed and ready for placement of the acetylene linker. Lithiation of the bromobenzoxazole 17 (n-butyllithium/THF) followed by immediate addition of 4-pentyne-1-al and reductive deoxygenation of the intermediate benzylic secondary alcohol provides the Group 2 benzoxazole target as shown in the shaded box (Scheme 4). The synthesis schemes for Group 1 and Group 2 compounds afford considerable flexibility by allowing in certain embodiments the ability to vary carbon chain length to ideally position the reactive azide and acetylene groups and introduce various alterations on the scaffolds to optimize binding to Mfa.

The second essential motif in BAR (and AgI/II), NITVK (SEQ ID NO:2), dictates the species specificity of *P. gingivalis* adherence to AgI/II and hence to oral streptococci. Comparing the sequence of this motif from AgI/II proteins that do and do not interact with Mfa (or *P. gingivalis*) indicated that Asn and Val were essential for activity. AgI/II proteins that did not interact with Mfa contained Gly and/or Pro at these positions, respectively. Furthermore, site specific alteration of Asn to Gly or Val to Pro in a full length active AgI/II rendered it inactive. To better understand the contribution of this motif to the Mfa-AgI/II interaction the inventors analyzed this motif using a combinatorial approach and determined the binding activity of peptides in which Asn and Val were substituted with all of the other common amino acids. Most amino acid substitutions had little effect on Mfa binding. Several were detrimental for binding, notably Pro and Gly, which is consistent with the site specific mutagenesis results discussed above. The surprising result was that some substitutions for Asn or Val promoted binding, as summarized in FIG. 4. These results provide additional information about the Mfa-AgI/II interacting interface. For example, substitution of basic amino acids for Asn improved *P. gingivalis* adherence. This suggests that Mfa may possess either a negatively charged group capable of charge interactions with the basic residues, or an electronegative atom(s) (e.g., carbonyl oxygen) that is capable of hydrogen bonding with Asn or basic amino acids. Consistent with this, the presence of the negatively charged residue aspartate in place of Asn was detrimental for binding. In addition, amino acids containing bulky hydrophobic R groups promoted Mfa binding to AgI/II when substituted for Val, suggesting that residues in this position may be accommodated by a hydrophobic pocket in Mfa. Thus, the association of the NITVK (SEQ ID NO:2) motif with Mfa appears to require both polar and hydrophobic interactions. In certain embodiments, the design of precursors for this motif therefore accommodated both polar and hydrophobic functional groups.

The design of NITVK (SEQ ID NO:2) mimics entails an oxazoline or oxazole structural scaffold (Scheme 5 in FIG. 5). Incorporated on to the scaffold is a lipophilic secondary butyl or isobutyl group which mimics the valine/isoleucine NITVK (SEQ ID NO:2) residues, a phenyl ring spacer which links the scaffold with a nitrogen or carbon atom bearing a full or positive charge, and an azide residue for the click coupling reaction. The scaffold, a planar oxazole or the more flexible oxazoline ring bears the closely juxtaposed atoms, which mimics the $Thr^{1184}$ residue flanking $Val^{1185}$ in the NITVK (SEQ ID NO:2) motif.

As shown in FIG. 5, the synthesis begins with the nitroaldol reaction of 3-methylnitrobutane with the appropriate meta-substituted benzaldehyde (R=$NH_2$, $NHCH_3$, $N(CH_3)_2$, $SO_2NH_2$, $CF_3$) catalyzed by TMG thereby affording the nitroalcohol 17. Reduction of 17 to the aminoalcohol 18 can be accomplished with catalytic hydrogenation ($H_2$ gas/palladium on carbon). The reaction of the ethoxyimidate of acetonitrile with aminoalcohol 18 will provide the oxazoline 19. Deprotonation of 19 with lithium diisopropylamide followed by direct treatment with p-toluenesulfonylazide should furnish the azidomethyl oxazoline 20. The binding affinity of the more 3-dimensional oxazoline 21 may be compared with the more rigid planar oxazole 21, and the conversion of 20 to 21 may be easily effected by treatment of 20 with nickel peroxide (Scheme 5). This compound (21) has already been successfully synthesized.

Figure 8:
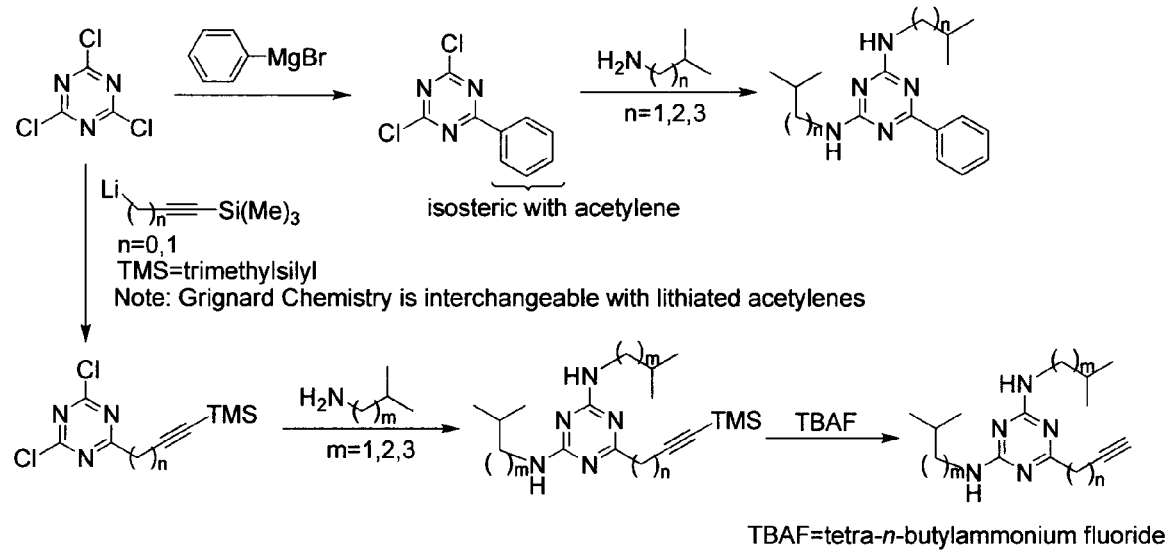
FIG. 8. Synthesis of acetylenic coupling partners.

For assembly of potential inhibitors, in situ click chemistry is carried out initially in 96 well microtiter plates. A typical reaction well contains 30 µM Mfa protein, 60-100 µM of the acetylene precursor and up to 400 µM of the azide precursor in PBS, pH7.4. Mfa protein is readily available from a high level pET30 expression construct (protein yield is ~50 mg Mfa per liter of culture). The crude reaction mixtures are analyzed by HPLC and mass spectroscopy to identify Mfa-catalyzed products (Whiting, M., Muldoon, J., Lin, Y.-C. et al. 2006. Inhibitors of HIV-1 protease using in situ click chemistry. Angew. Chem. Int. Ed. 45:1435-1439). This reaction mixture is compared to control reactions that contain precursor compounds in the absence of Mfa to monitor the background rate of the cycloaddition reaction, and a reaction containing BSA to determine the extent of catalysis that occurs in the presence of a non-specific protein. To confirm that the products arise from Mfa-mediated catalysis, the reactions are repeated in the presence of the known inhibitory peptide. Inhibition of product formation in the presence of peptide confirms that formation of the product required the Mfa active site. An example of a click cycloaddition reaction between the oxazole-scaffolded azide 20 and the Group 1 pyrimidine-scaffolded VXXLL (SEQ ID NO:1) inhibitor (outlined in Scheme 1) is detailed in Scheme 6 (see FIG. 5). Typically, terminal acetylenes are very reactive toward alkyl or aryl azide giving triazoles. When the coupling partners are incubated the presence of the protein, a thermal cycloaddition reaction should ensue, and under favorable binding conditions should afford the coupled product triazole (Manetsch, R., Krazinski, Z., Raushel, J., Taylor, P., Sharpless, K. B. and Kolb, H. C. 2004. In situ click chemistry: enzymes made to their own specifications. J. Am. Chem. Soc. 126:12809-12818). FIGS. 7 and 8 further outline the synthesis of the azide and acetylene coupling partners.

Bioactivity of Mfa-Catalyzed Products. The Mfa-catalyzed products described above are analyzed initially using a series of in vitro binding and biofilm inhibition assays. For all assays involving intact bacteria, the toxicity of the click compounds is determined by growing planktonic cultures in the presence of increasing concentrations of the inhibitor and comparing growth to that in medium alone.

The kinetics of Mfa binding to inhibitors is carried out using a plate-based assay. Increasing amounts of the click compounds is immobilized onto microtiter plates either by adsorption or chemical cross-linking. If necessary, the click compounds are first derivatized with any of the common chemical cross-linking functional groups and covalently attached to an appropriately activated plate. Bound compound are then incubated with purified Mfa and bound protein is visualized using rabbit polyclonal anti-Mfa antibody and anti-rabbit conjugate. Specificity of binding is confirmed by the addition of the existing peptide inhibitor, as discussed above. Similarly, the kinetics of inhibition of *P. gingivalis* adherence to streptococci or purified AgI/II is determined by immobilizing *S. gordonii* DL1 cells (or AgI/II) onto microtiter plates (*S. gordonii* DL1 readily interacts with *P. gingivalis* and was the source of the AgI/II used in the previous structure function studies) and incubating with intact *P. gingivalis* in the presence of increasing concentrations of the potential inhibitors. Bound *P. gingivalis* is quantified using the anti-Mfa antibodies as described above. These initial tests are also carried out on the individual click precursors as they are synthesized (e.g., compound 21 described above).

The plate assays above allow a quick examination of the kinetics of Mfa binding and inhibition of bacterial adherence. To determine if the Mfa-catalyzed compounds selected above inhibit the formation of *P. gingivalis* biofilms, or alternatively are capable of disrupting a pre-existing biofilm, dual species *P. gingivalis-S. gordonii* biofilms are grown and analyzed as previously described by Daep et al. (Daep, C. A., James, D. M., Lamont, R. J. and Demuth, D. R. 2006. Structural Characterization of Peptide-Mediated Inhibition of *P. gingivalis* Biofilm Formation. Infect. Immun. 74: 5756-5762; Daep, C. A., Lamont R. J. and Demuth, D. R. 2008. Interaction of *P. gingivalis* with oral streptococci requires a motif that resembles the eukaryotic nuclear receptor box protein-protein interaction domain. Infect. Immun. 76:3272-3280) using an open flow biofilm culture system. To determine if the inhibitors are capable of disrupting existing *P. gingivalis-streptococcal* biofilms, pre-formed biofilms are incubated with medium containing the inhibitor and analyzed as above. The inhibitors identified from the assays above are analyzed for in vivo efficacy in preventing *P. gingivalis* colonization in a mouse model of periodontitis.

Figure 6:
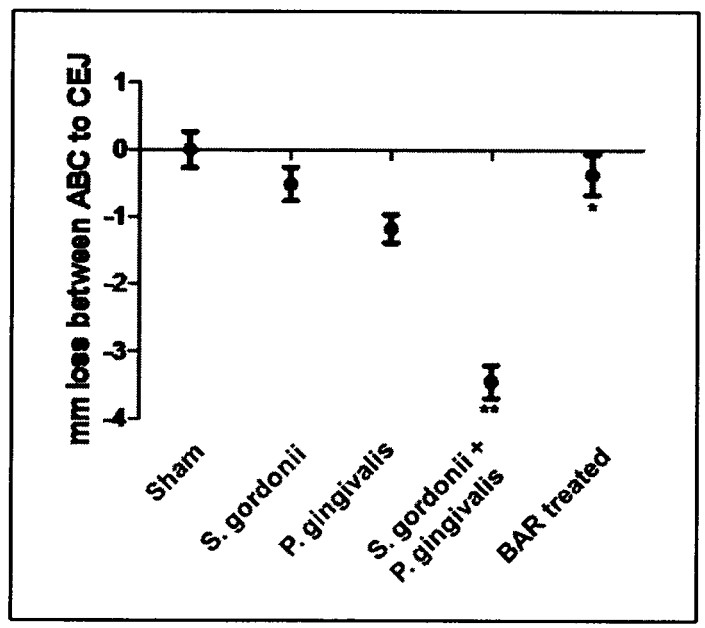
FIG. 6. Alveolar bone loss induced in Balb/cByJ mice in the presence and absence of BAR peptide. Sham infected animals were inoculated with CMC slurry without bacteria.

To determine how effectively the inhibitors limit or prevent *P. gingivalis* colonization in vivo, a modified Baker mouse model of periodontitis is used. The model is modified by first infecting with and establishing *S. gordonii* in the oral cavity of Balb/cByJ mice then subsequently challenging with *P. gingivalis*. In the presence of *S. gordonii*, a persistent infection of *P. gingivalis* (detected by 16S rDNA PCR 47 days post infection) can be established using an inoculum of $10^7$ cfu. As shown in FIG. 6, low levels of bone resorption occurred in animals infected with either *S. gordonii* or $10^7$ cfu *P. gingivalis* alone. However, significantly greater levels of bone loss occurred in mice infected with both organisms, but this was reduced to near sham infected levels when BAR peptide was added to the inoculum, suggesting that BAR peptide inhibited *P. gingivalis* colonization. Thus, preventing *P. gingivalis* colonization of mice reduces alveolar bone loss.

Initial experiments evaluate the effectiveness of click compounds in preventing *P. gingivalis* colonization during the initial infection period. Animals are infected with a slurry of carboxymethylcellulose containing $10^7$ *P. gingivalis* cells in the presence or absence of a concentration range of inhibitor. The presence and persistence of *P. gingivalis* is followed by culture plating and 16S rDNA PCR techniques. In addition, the extent of alveolar bone loss is determined for all groups at the termination of the experiment as a measure of clinical outcome. Bone loss is determined by measuring the distance from the cementum-enamel junction to the alveolar bone crest as previously described (Wang, M., Shakhatreh, M. A., James, D., Liang, S., Nishiyama, S., Yoshimura, F., Demuth, D. R. and Hajishengallis, G. 2007. Fimbrial proteins of *P. gingivalis* mediate in vivo virulence and exploit TLR2 and complement receptor 3 to persist in macrophages. J. Immunol. 15:2349-2358). Animals infected in the presence of inhibitors that block *P. gingivalis* adherence and colonization exhibit significantly lower levels of bone loss.

Examples 2-8 describe the synthesis of compounds that can be used to prepare compounds of the invention as well as compounds that are useful for modeling such compounds. Example 9 describes the biological testing of compounds of the examples. Example 10 describes how the compounds of the invention can be prepared.

General Methods of Examples 2-8

Solvents and reagents were ACS grade and used as commercially supplied. Tetrahydrofuran was distilled from a mixture of sodium and benzophenone prior to its use. Analytical thin-layer chromatography (TLC) utilized 0.25 mm pre-cut glass-backed plates (Merck, Silica Gel 60 $F_{254}$). Thin-layer chromatograms were visualized during chromatographic and extraction runs by rapidly dipping the plates in anisaldehyde/ethanol/sulfuric acid stain or phosphomolybdic acid/ethanol stain and heating (hot plate). Column chromatography was carried out using silica gel 60 (E. Merck 9385, 235-400 mesh/flash) or silica gel 62 (Mallinckrodt 6551, 60-200 mesh/gravity). Melting points were taken on a Thomas Hoover apparatus. Extracts and chromatographic fractions were concentrated with a Büchi rotavapor under water aspirator vacuum. Nuclear magnetic resonance ($^1$H and $^{13}$C NMR) spectra were recorded with Varian INOVA 500 or VNMRS 400 instruments using $CDCl_3$ as a solvent and internal standard Infrared spectra (Fourier transform infrared spectroscopy, FTIR) were recorded with a Perkin-Elmer Spectrum 100 instrument.

EXAMPLE 2

Preparation of Compound 25

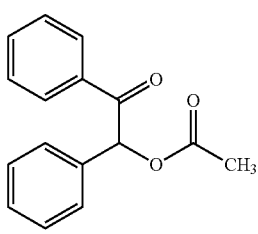

24

2-Oxo-1,2-diphenylethyl acetate (24): Benzoin 23 (2.0 g, 9.40 mmol) was dissolved in acetic anhydride (15 mL, 158.70 mmol) followed by the addition of two drops of sulfuric acid which resulted in a pale yellow color. The reaction mixture was then stirred under a nitrogen atmosphere at room temperature (72 h) while monitoring its progress by TLC. The reaction mixture was then dissolved in water and extracted with dichloromethane (3×40 mL). The dichloromethane layer was then dried over anhydrous sodium sulfate. After removal of the drying agent by filtration and removal of the solvent by rotary evaporation, the product was found to be of acceptable purity as evidenced by $^1$H NMR and TLC, Rf: 0.2 (hexane/ethyl acetate, 2:1): mp 83-85° C. (Lit. 85-87° C.).

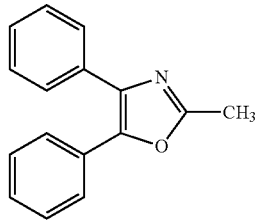

25

2-Methyl-4,5-diphenyloxazole (25): 2-Oxo-1,2-diphenylethyl acetate 24 (0.20 g, 0.79 mmol) was dissolved in DMF (10 mL). Thiourea was then added and the reaction was refluxed (160° C., oil bath) under nitrogen atmosphere. As the reaction progressed, the color changed from colorless to a light yellow-orange and had an odorous smell. The reaction was monitored by TLC and when complete, the reaction mixture was dissolved in dichloromethane (40 mL) and then washed with water (3×30 mL). The dichloromethane layer was separated and dried over anhydrous sodium sulfate. Removal of the drying agent by filtration and rotary evaporation of the solvent gave a crude oil that was purified by flash chromatography on silica gel (dichloromethane) to provide 25 (74%): Rf: 0.098 (hexane/ethyl acetate, 2:1); FTIR 2920.50; 1220.30; 1502.00; 1588.24 cm$^{-1}$; $^1$H NMR (400 MHz, $CDCl_3$) δ: 2.617 (s, 3H); 7.25-7.66 (m, 10H, aromatic); $^{13}$C NMR (100 MHz, $CDCl_3$) δ 160.35, 145.41, 134.82, 126.46-132.14, 13.92; HRMS calcd for $C_{16}H_{13}NO$ (M+H)$^+$ 236.1075, Found: 236.1077.

EXAMPLE 3

Preparation of Compounds 27a, 27b and 27c

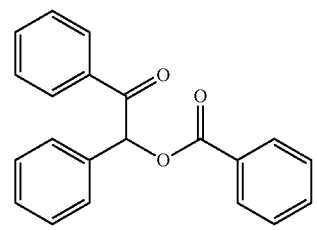

26a

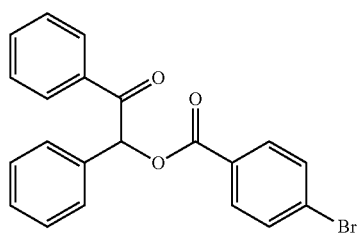

26b

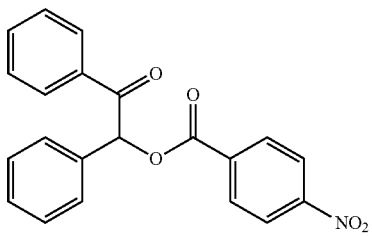

26c

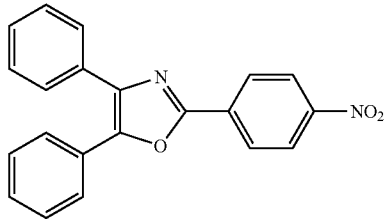

27c

General procedure for the preparation of benzoin esters (26a, 26b, 26c): Benzoin (1 eq) was dissolved in pyridine (10 mL) followed by cooling the solution to 0° C. (ice water bath). The aroyl chloride (1 eq, benzoyl chloride, 4-bromobenzoyl chloride, 4-nitrobenzoyl chloride) was then added dropwise to the stirred solution while cooling. The reaction flask was then capped, and after stirring 30 minutes, the cooling bath was removed. The reaction mixture was stirred (18 h) while monitoring by TLC. After the starting materials were consumed, the reaction mixture was dissolved in dichloromethane (150 mL) and washed with 5% aqueous HCl (5×100 mL). The organic layer was then separated and dried over anhydrous sodium sulfate. Flash chromatography on silica gel (hexane/ethyl acetate, 9:1) afforded esters 26a, 26b and 26c as crystalline solids in 87%, 32% and 45% yield respectively. 2-oxo-1,2-diphenylethyl benzoate (26a): m.p. 123-126° C. (Lit. 125-126° C.), 2-oxo-1,2-diphenylethyl-4-nitrobenzoate (26c): mp. 126-128° C. (Lit. 126-127° C.). 2-Oxo-1,2-diphenylethyl-4-bromobenzoate (26b): Rf: 0.24 (hexane/ethyl acetate, 9:1); FTIR 1708.25, 1690.56, 1498.22, 1449.91 cm$^{-1}$; $^1$H NMR (400 MHz, CDCl$_3$) δ: 7.13 (s, 1H); 7.36-8.04 (m, 14H); $^{13}$C NMR (100 MHz, CDCl$_3$) δ: 193.45, 165.35, 128.37-134.61, 78.22; HRMS calcd for C$_{21}$H$_{15}$BrO$_3$ (M+Li)$^+$ 401.0365. Found: 401.0369.

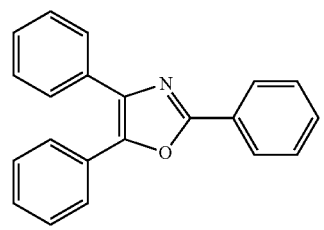

27a

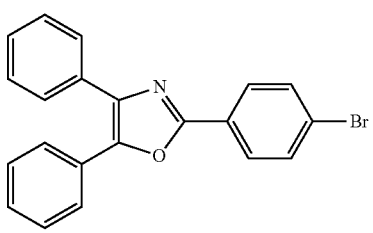

27b

General procedure for the preparation of triaryl oxazole formation (27a, 27b, 27c): The benzoin ester (1 eq, 26a, 26b, 26c) is dissolved in glacial acetic acid (8 mL) Ammonium acetate (15 eq) was then added and the reaction mixture was refluxed (118° C., oil bath) under nitrogen (1.5 h). The reaction was monitored by TLC and when complete, the reaction mixture was dissolved in diethyl ether (200 mL) and washed with 6% aqueous sodium hydroxide solution (4×100 mL). The dichloromethane layer was then separated and dried over anhydrous sodium sulfate. Removal of the drying agent by filtration and rotary evaporation of the solvent gave a crude oil that was purified by flash chromatography on silica gel (hexane/ethyl acetate, 9:1) to furnish the triaryl oxazoles 27a (31%, mp 116-118° C., Literature: 116-117° C.), 27c (14%, mp 144-145° C.; Literature: 145-146° C.) and 27b in 31%, 14%, and 5% yield respectively. 2-(4-bromophenyl)-4,5-diphenyloxazole (27b): Rf: 0.52 (hexane/ethyl-acetate, 9:1); FTIR 1161.00, 1475.00, 1605.12 cm-1; $^1$H NMR (400 MHz, CDCl$_3$) δ: 7.416-8.06 (m, 14H); $^{13}$C NMR (100 MHz, CDCl$_3$) δ: 159.26, 145.87, 136.87, 124.93-132.29; HRMS calcd for C$_{21}$H$_{14}$BrNO (M+H)$^+$ 376.0337. Found: 376.0328.

EXAMPLE 4

Preparation of Compounds 34 and 35

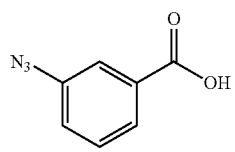

28

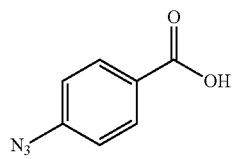

29

General Procedure for the preparation of 3- and 4-azidobenzoic acid (28, 29): The 3-amino- or 4-aminobenzoic acid (1 eq) was dissolved in 10% aqueous HCl solution and cooled to 0° C. (ice bath). Aqueous sodium nitrite (1.1 eq, 20%) was then added and the reaction mixture was allowed to stir at room temperature (15 min). A 20% aqueous solution of sodium azide (1.2 eq) then was added at room temperature which resulted in a vigorous reaction and creating a foaming precipitate which filled the headspace of the reaction flask. The foam precipitate, which was the azidobenzoic acid product, was collected by vacuum filtration while washing the filter cake with water and excess solvent was removed by rotary evaporation. The slightly yellow-white solids 4-azidobenzoic Acid: mp 189-190° C., Literature: 188.5-190° C. and 3-azidobenzoic Acid: mp 176-178° C., Literature: 176-177° C. were of sufficient purity to use in the next step.

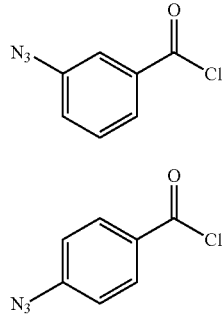

General Procedure for the preparation of 3- and 4-azidobenzoyl chloride (30, 31): The azidobenzoic acid 28 or 29 (1 eq) was dissolved in thionyl chloride (4.5 eq). The mixture was heated to reflux (75° C.), and allowed to stir (5 h). The reaction mixture was then allowed to stir overnight at room temperature. Thionyl chloride was then removed by adding dichloromethane (10 mL) and concentrating with the rotary evaporator under aspirator vacuum. The addition of dichloromethane and vacuum rotary evaporation was repeated (3×) to give the acid chloride as an oil. The azidobenzoyl chloride was used in esterification step without further purification.

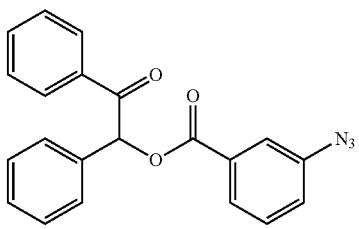

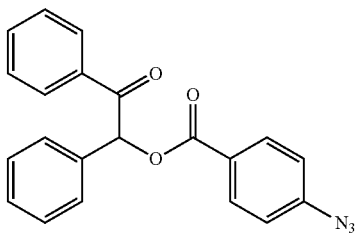

General Procedure for the preparation of 2-oxo-1,2-diphenylethyl-3-azidobenzoate (33) and 2-oxo-1,2-diphenylethyl-4-azidobenzoate (32): Benzoin (1 eq), triethylamine (1 eq), and 4-dimethylaminopyridine (0.1 eq) were dissolved in dichloromethane (10 mL) at 0° C. (ice water bath). The azidobenzoyl chloride (1 eq) in dichloromethane (5 mL) was gradually introduced into the reaction flask while stirring. The reaction mixture was allowed to stir (3 h) at room temperature while monitoring by TLC. Upon completion of the reaction as evidenced by TLC, the reaction mixture was dissolved in diethyl ether (100 mL) and washed with 5% aqueous HCl solution (4×50 mL) followed by 5% aqueous sodium bicarbonate (2×100 mL). The organic layer was separated and dried over anhydrous sodium sulfate. Removal of the drying agent by filtration and rotary evaporation of the solvent gave a crude solid that was purified by flash chromatography on silica gel (hexane/EtOAc, 4:1) to obtain 32 and 33 in 72% and 80% yield.

2-oxo-1,2-diphenylethyl-4-azidobenzoate (32): Rf: 0.42 (hexane/ethyl acetate, 4:1); FTIR 2118.00, 1174.79, 1710.42, 1693.73, 1448.18, 1504.39 cm$^{-1}$; $^1$H NMR: (400 MHz, CDCl$_3$) δ: 6.96 (s, 1H); 6.99-7.33 (m, 14H); 7.90-7.92 (d, 2H, J=7.99); 8.01-8.04 (d, 2H); $^{13}$C NMR (100 MHz, CDCl$_3$) δ: 193.62, 165.20, 145.29, 118.81-145.20, 78.06; HRMS calcd for C$_{21}$H$_{15}$N$_3$O$_3$ (M+H)$^+$ 358.1192. Found: 358.1195.

2-oxo-1,2-diphenylethyl-3-azidobenzoate (33): Rf: 0.53 (hexane/ethylacetate, 4:1); FTIR 2124.85, 1299.51, 1711.90, 1695.45, 1482.43, 1448.61 cm$^{-1}$; $^1$H NMR: (400 MHz, CDCl$_3$) δ: 7.00 (s, 1H); 7.08-7.90 (m, 14H); $^{13}$C NMR (100 MHz, CDCl$_3$) δ: 193.42, 165.20, 120.16-140.62, 78.33; HRMS calcd for C$_{21}$H$_{15}$N$_3$O$_3$ (M+Li)$^+$ 364.1273. Found: 364.1266.

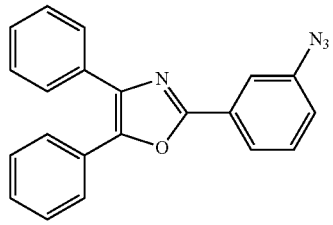

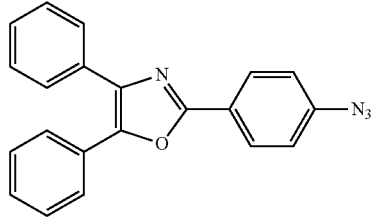

General Procedure for the preparation of 2-(3-azidophenyl)-4,5-diphenyloxazole (35) and 2-(4-azidophenyl)-4,5-diphenyloxazole (34): The azido benzoic esters 32 or 33 (1 eq) and ammonium acetate (15 eq) were combined in glacial acetic acid (10 mL). The mixture was allowed to react at reflux (118° C.) for 2 hours under an atmosphere of nitrogen. The reaction mixture was monitored by TLC and when complete, the reaction mixture was dissolved in diethyl ether (110 mL) and washed with NaOH solution (3×100 mL). The diethyl ether layer was separated and dried over anhydrous sodium sulfate. Removal of the drying agent by filtration and rotary evaporation of the solvent gave a crude oil that was purified by flash chromatography on silica gel (hexane/ethylacetate, 4:1) to obtain 34 and 35 in 61% and 80% yield.

2-(4-azidophenyl)-4,5-diphenyloxazole (34): Rf: 0.60 (hexane/ethyl acetate, 4:1); FTIR: 2088.97, 1278.93, 1608.72, 1493.77, 1087.95 cm$^{-1}$; $^1$H NMR: (500 MHz, CDCl$_3$) 7.21-8.13 (m, 14H, aromatic); $^{13}$C NMR (125 MHz, CDCl$_3$) δ: 159.46, 145.61, 142.26, 136.47, 119.34-132.01; HRMS calcd for C$_{21}$H$_{14}$N$_4$O (M+H)$^+$ 339.1246. Found: 339.1243.

2-(3-azidophenyl)-4,5-diphenyloxazole (35): Rf: 0.53 (hexane/ethyl acetate, 4:1); FTIR: 2146.37, 1276.93, 1590.12, 1590.35 cm$^{-1}$; $^1$H NMR: (400 MHz, CDCl$_3$) δ: 7.09-7.94 (m, 14H, aromatic); $^{13}$C NMR (100 MHz, CDCl$_3$)

δ: 159.09, 145.96, 140.87, 136.85, 116.84-132.25; HRMS calcd for $C_{21}H_{14}N_4O$ (M+H)$^+$ 339.1246. Found: 339.1241.

EXAMPLE 5

Preparation of Compounds 39a and 39b

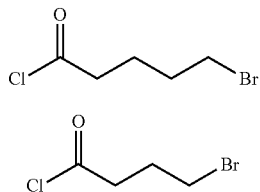

General procedure for the preparation of acid chlorides (36a, 36b): 5-Bromovaleric acid (1 eq) or 4-bromobutyric acid (1 eq) was dissolved in thionyl chloride (4.5 eq). The reaction mixture was then refluxed (75° C., oil bath) under nitrogen atmosphere overnight. The excess thionyl chloride was removed by adding dichloromethane (25 mL) and removing using a rotary evaporator under aspirator vacuum. The addition of the dichloromethane and rotary evaporation was repeated (3×) which yielded the acid chloride as an oil. The 5-bromovaleryl chloride 36a or the 4-bromobutyryl chloride 36b were used without further purification in the next step.

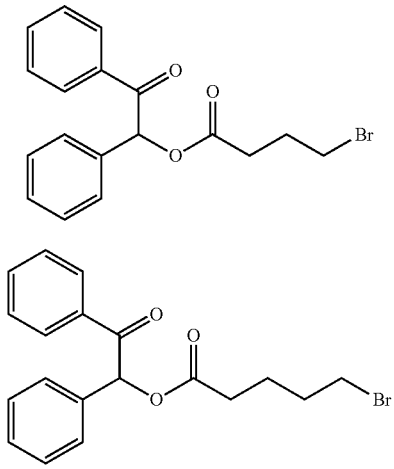

General Procedure for the preparation of the bromoacyl esters (37a, 37b): Benzoin (1 eq) was dissolved in pyridine (12 mL) followed by cooling the solution to 0° C. (ice water bath). The acid chloride 36a or 36b (1 eq) was then added dropwise to the stirred solution while cooling. The reaction flask was capped, and after 30 minutes, the cooling bath was removed. The reaction mixture was stirred (4 h) while monitoring by TLC. After the starting materials were consumed, the reaction mixture was then dissolved in dichloromethane (300 mL) and washed with 5% aqueous HCl (5×120 mL). The organic layer was then separated and dried over anhydrous sodium sulfate. Flash chromatography on silica gel (hexane/ethyl acetate, 6:1) afforded esters 37a and 37b as oils in 70% and 23% yield respectively: 2-Oxo-1,2-diphenylethyl-4-bromobutanoate (37a): Rf: 0.49 (hexane/ethylacetate, 4:1); FTIR: 3063.60, 1708.60, 1692.03, 1588.70, 1531.70 cm$^{-1}$; $^1$H NMR (400 MHz, CDCl$_3$) δ: 2.21-2.23 (t, 2H); 2.60-2.69 (m, 2H); 3.45-3.47 (t, 2H); 6.85 (s, 1H); 7.28-8.01 (m, 10H); $^{13}$C NMR (100 MHz, CDCl$_3$) δ: 193.66, 172.08, 134.56, 133.57, 128.70-129.43, 77.85, 32.55, 32.34, 27.83 2-oxo-1, 2-diphenylethyl-5-bromopentanoate (37b): Rf: 0.47 (hexane/ethyl acetate, 4:1); FTIR: 1734.38, 1693.88, 1597.38, 1448.37 cm$^{-1}$; $^1$H NMR (400 MHz, CDCl$_3$) δ: 1.81-1.87 (m, 2H); 1.91-1.98 (m, 2H); 2.44-2.59 (m, 2H); 3.40-3.43 (t, 2H); 6.85 (s, 1H), 7.35-7.93 (m, 10H); $^{13}$C NMR (100 MHz, CDCl$_3$) δ: 193.75, 172.63, 134.59, 133.49, 128.07-128.83, 60.25, 44.55, 33.09, 31.76, 23.38.

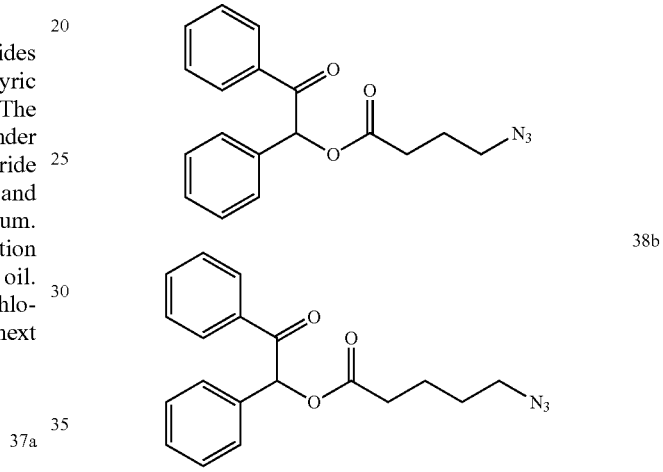

General procedure for the conversion of the brominated esters 37a, 37b to azido esters (38a, 38b): The halogenated ester 37a or 37b (1 eq) was dissolved in DMF. Sodium azide (1.1 eq) was then added and the reaction mixture was heated (80° C., oil bath) under a nitrogen atmosphere (4 h). The reaction mixture was monitored by TLC and when complete, the DMF was removed under high vacuum. The crude oil was purified by flash chromatography on silica gel (hexane/ethylacetate, 9:1) to obtain 38a and 38b in 85% and 56% yield respectively:

2-oxo-1,2-diphenylethyl-4-azidobutanoate (38a): Rf: 0.44 (hexane/ethylacetate, 4:1); FTIR: 2096.16, 1448.47, 1734.69, 1693.83, 1580.74, 1496.07 cm$^{-1}$; $^1$H NMR (500 MHz, CDCl$_3$) δ: 1.82-1.92 (t, 2H); 2.41-2.60 (m, 2H); 3.28-3.38 (t, 2H); 6.82 (s, 1H); 7.25-7.98 (m, 10H, aromatic); $^{13}$C NMR (125 MHz, CDCl$_3$) δ: 193.65, 172.23, 134.55, 133.56, 128.69-129.19, 77.86, 50.54, 30.95, 24.33; HRMS calcd for $C_{18}H_{17}N_3O_3$ (M+H)$^+$ 324.1348. Found: 324.1346.

2-oxo-1,2-diphenylethyl-5-azidopentanoate (38b): Rf: 0.22 (hexane/ethyl acetate, 4:1); FTIR 2092.58, 1224.81, 1734.84, 1694.21, 1597.46, 1448.81 cm$^{-1}$; $^1$H NMR: (500 MHz, CDCl$_3$) δ: 1.52-1.61 (m, 2H); 1.62-1.71 (m, 2H); 2.32-2.49 (m, 2H); 3.14-3.22 (t, 2H); 6.782 (s, 1H); 7.24-7.85 (m, 10H); $^{13}$C NMR (125 MHz, CDCl$_3$) δ: 193.76, 172.64, 134.60, 133.55, 128.66-129.36, 77.66, 51.02, 33.33, 28.13, 22.04; HRMS calcd for $C_{19}H_{19}N_3O_3$ (M+H)$^+$ 338.1505. Found: 338.1500.

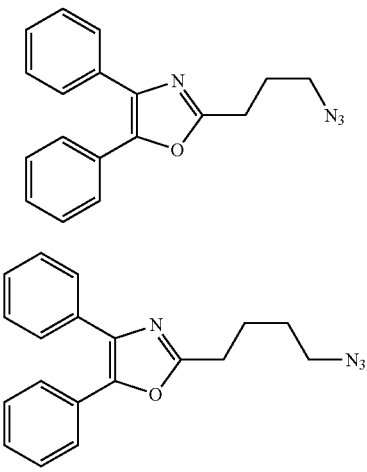

39a

39b

General procedure for the preparation of the azidoalkyl oxazoles (39a, 39b): The azido ester 38a, 38b (1 eq) was dissolved in glacial acetic acid (10 mL). Ammonium acetate (15 eq) was then added and the reaction mixture was refluxed (118° C., oil bath) under a nitrogen atmosphere (2 h). The reaction mixture was monitored by TLC, and when complete as evidenced by the disappearance of the ester, the reaction mixture was dissolved in diethyl ether (100 mL) and washed with aqueous sodium hydroxide (3×100 mL). The organic layer was separated and dried over anhydrous sodium sulfate. Flash chromatography on silica gel (hexane/ethylacetate, 8:1) afforded 39a and 39b in 64% and 81% yield;

2-(3-azidopropyl)-4,5-diphenyloxazole (39a): Rf: 0.30 (hexane/ethylacetate, 8:1); FTIR 2094.21, 1218.91, 2933.26, 1570.34, 1501.98, 1218.91 cm$^{-1}$; $^1$H NMR: (500 MHz, CDCl$_3$) δ: 2.16-2.19 (m, 2H); 3.02-3.06 (t, 2H); 3.49-3.51 (t, 2H); 7.35-7.67 (m, 10H); $^{13}$C NMR (125 MHz, CDCl$_3$) δ: 162.68, 145.69, 134.22, 126.54-131.34, 50.55, 26.31, 25.18; HRMS calcd for C$_{18}$H$_{16}$N$_4$O (M+H)$^+$ 305.1402. Found: 305.1407.

2-(4-azidobutyl)-4,5-diphenyloxazole (39b): Rf: 0.50 (hexane/ethyl acetate, 4:1); FTIR 2936.78, 2091.06, 1218.94, 1570.01, 1501.95, 1157.14 cm$^{-1}$; $^1$H NMR: (500 MHz, CDCl$_3$) δ: 1.77-1.80 (m, 2H); 1.96-2.0 (m, 2H); 2.92-2.95 (t, 2H); 3.36-3.39 (t, 2H); 7.336-7.668 (m, 10H); $^{13}$C NMR (125 MHz, CDCl$_3$) δ: 162.99, 145.35, 132.23, 126.47-128.92, 51.04, 28.35, 27.65, 24.27; HRMS calcd for C$_{19}$H$_{18}$N$_4$O (M+H)$^+$ 319.1559. Found: 319.1564.

EXAMPLE 6

Preparation of Compound 42

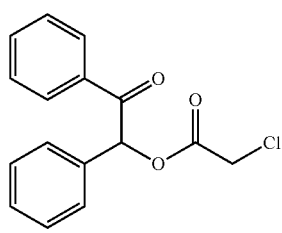

40

2-Oxo-1,2-diphenylethyl-2-chloroacetate (40): Benzoin (0.50 g, 2.37 mmol) and 4-dimethylaminopyridine (0.29 g, 2.37 mmol) were dissolved in dichloromethane (20 mL) and the solution was allowed to stir at 0° C. Chloroacetyl chloride (0.21 mL, 2.60 mmol) was added dropwise by syringe. The reaction mixture was then stirred under nitrogen at 0° C. (4 h) while monitoring by TLC. Upon completion of the reaction, the reaction mixture was dissolved in diethyl ether (100 mL) and washed with water (2×90 mL), 5% aqueous HCl (1×90 mL), and 5% aqueous sodium bicarbonate (1×90 mL). The diethyl ether layer was separated and dried over anhydrous sodium sulfate. After removal of the drying agent by filtration and removal of solvent by rotary evaporation, the product chloroacetyl ester 40 was obtained in 95% yield and found to be of reasonable purity as evidenced by $^1$H NMR and TLC. Rf: 0.51 (hexane/ethylacetate, 4:1); FTIR 2960.22, 1734.54, 1694.12, 1597.47, 1495.83, 1224.81 cm$^{-1}$; NMR (500 MHz, CDCl$_3$) δ: 7.25-7.91 (m, 10H); 6.94 (s, 1H); 3.96-4.11 (dd, 2H); $^{13}$C NMR (125 MHz, CDCl$_3$) δ: 192.62, 167.91, 128.71-134.17, 78.75, 50.11

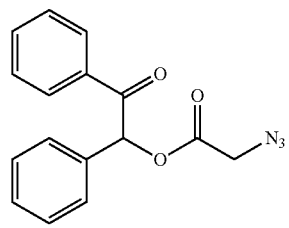

41

2-Oxo-1,2-diphenylethyl-2-azidoacetate (41): 2-oxo-1,2-diphenylethyl-2-chloroacetate 40 (0.72 g, 2.50 mmol) is dissolved in DMF (5 mL). Sodium azide (0.18 g, 2.77 mmol) was then added and the reaction mixture was heated (80° C., oil bath) under nitrogen (4 h). The reaction mixture was monitored by TLC and when complete, the DMF was removed from the reaction mixture by rotary evaporation and then high vacuum. The crude oil was purified by flash chromatography on silica gel (hexane/ethyl acetate, 9:1) to obtain the azido ester 41 in 22% yield: Rf: 0.49 (hexane/ethyl acetate, 4:1); FTIR 2104.56, 1173.01, 1747.90, 1692.58, 1597.22, 1448.76 cm-1; $^1$H NMR: (500 MHz, CDCl$_3$) δ: 7.38-7.94 (m, 10H); 6.97 (s, 1H); 4.03-4.10 (dd, 2H); $^{13}$C NMR (125 MHz, CDCl$_3$) δ: 192.72, 167.99, 128.44-134.99, 78.79, 50.09; HRMS calcd for C$_{16}$H$_{13}$N$_3$O$_3$(M+Li)$^+$ 302.1117, Found 302.1121.

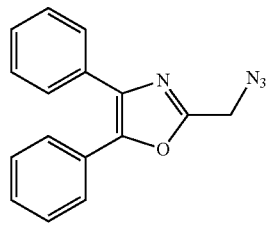

42

2-(Azidomethyl)-4,5-diphenyloxazole (42): 2-Oxo-1,2-diphenylethyl-2-azidoacetate 41 (0.14 g, 0.48 mmol) was dissolved in glacial acetic acid (3.0 mL). Ammonium acetate (0.57 g, 7.40 mmol) was then added and the reaction mixture was refluxed (118° C., oil bath) under a nitrogen atmosphere (2 h). The reaction was monitored by TLC and when it was complete, the reaction mixture was dissolved in diethyl ether (100 mL) and washed with 7% aqueous sodium hydroxide solution (3×100 mL). The diethyl ether layer was separated and dried over anhydrous sodium sulfate. Removal of the drying agent by filtration and rotary evaporation of the solvent gave a crude oil that was purified by flash chromatography on silica gel (hexane:ethylacetate, 8:1) to provide the azidomethyl oxazole 42 in 46% yield: Rf: 0.58 (hexane/ethylacetate, 4:1); FTIR 2098, 1444.19, 1569.48, 1604.78, 1251.13 cm$^{-1}$; $^1$H NMR (400 MHz, CDCl$_3$) δ: 4.44 (s, 2H); 7.18-7.59 (m, 10H; $^{13}$C NMR (125 MHz, CDCl$_3$) δ: 157.23, 146.77, 135.52, 126.69-131.80, 46.75; HRMS calcd for C$_{16}$H$_{13}$N$_4$O (M+H)$^+$ 277.1089, Found: 277.1090.

EXAMPLE 7

Preparation of Compound 45

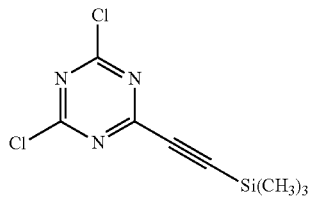

43

2,4-Dichloro-6-((trimethylsilypethynyl)-1,3,5-triazine (43): Trimethylsilylacetylene (0.50 mL, 3.51 mmol) was dissolved in freshly-distilled anhydrous THF (3 mL). n-butyllithium (2.20 ml, 3.52 mmol) was then added dropwise by syringe under an atmosphere of argon. The reaction mixture was stirred (10 min) under argon atmosphere at 0° C. (ice bath). The lithiotrimethylsilylacetylene 25 was then cannulated over a 30 minute period into a solution of cyanuric chloride (24, 0.65 g, 3.52 mmol) dissolved in anhydrous THF (4 mL) The reaction mixture was stirred under nitrogen at 0° C. (ice bath). A sample was taken from the reaction mixture and was found to be the product as evidenced by $^1$H NMR and $^{13}$C NMR: $^1$H NMR (400 MHz, CDCl$_3$) δ: 0.00 (s, 9H); $^{13}$C NMR (100 MHz, CDCl$_3$) δ: 172.93, 161.97, 107.07, 99.77, 0.00

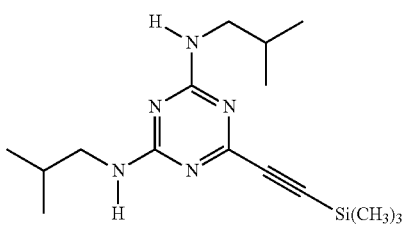

44

N$^2$,N$^4$-diisobutyl-6-((trimethylsilyl)ethynyl)-1,3,5-triazine-2,4-diamine (44): Isobutylamine (0.73 mL, 7.38 mmol) and diisopropylethylamine (1.53 mL, 8.78 mmol) were dissolved THF (2 mL) 2,4-dichloro-6-((trimethylsilyl)ethynyl)-1,3,5-triazine (above) 43 (0.85 g, 3.45 mmol) was then added by syringe and the reaction mixture was left to react at room temperature (12 h) while monitoring the progress by TLC. When complete, the reaction mixture was dissolved in dichloromethane (150 mL) and then washed with water (3×80 mL) The dichloromethane layer was separated and dried over anhydrous sodium sulfate. Removal of the drying agent by filtration and rotary evaporation of the solvent gave a crude solid that was purified by flash chromatography on silica gel (hexane/ethylacetate, 9:1) to afford 44 (1.3%): Rf: 0.79 (hexane/ethylacetate, 2:1). $^1$H NMR (400 MHz, CDCl$_3$) δ: 0.67-0.69 (d, 12H), 1.57-1.66 (m, 1H), 2.91-3.02 (dt, 4H); $^{13}$C NMR (100 MHz, CDCl$_3$) δ: 165.32, 157.15, 101.47, 58.67, 31.45, 28.78, 20.65, 0.00

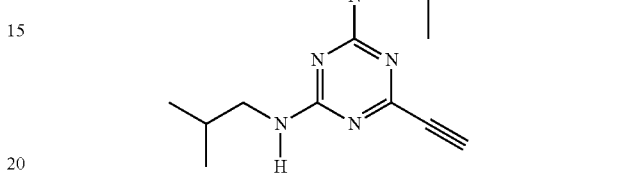

45

6-Ethynyl-N$^2$,N$^4$-diisobutyl-1,3,5-triazine-2,4-diamine (45): N2,N4-diisobutyl-6-((trimethyl-silyl)ethynyl)-1,3,5-triazine-2,4-diamine (27, 14.5 mg, 0.045 mmol) was dissolved in THF (1 mL). Tetrabutylammonium fluoride (0.59 mL, 2.04 mmol) was then added and the reaction mixture was left to react at room temperature (30 min). The reaction was monitored by TLC and when complete, the solvent was removed from the reaction mixture by rotary evaporation to give a crude solid that was purified by flash chromatography on silica gel (hexane/ethyl acetate, 2:1) to afford 45 in 12% yield. 6-ethynyl-N2,N2-diisobutyl-1,3,5-triazine-2,4-diamine (28): Rf: 0.14 (hexane/ethylacetate, 2:1). $^1$H NMR (400 MHz, CDCl$_3$) δ: 0.92-0.94 (d, 12H), 2.15-2.16 (d, 4H), 3.21-3.27 (m, 2H), 5.29 (s, 1H).

EXAMPLE 8

Preparation of Compound 46

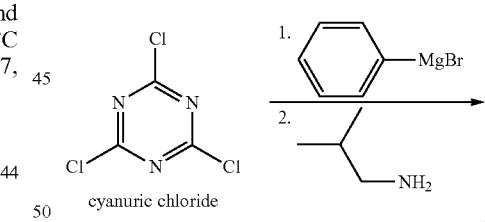

cyanuric chloride

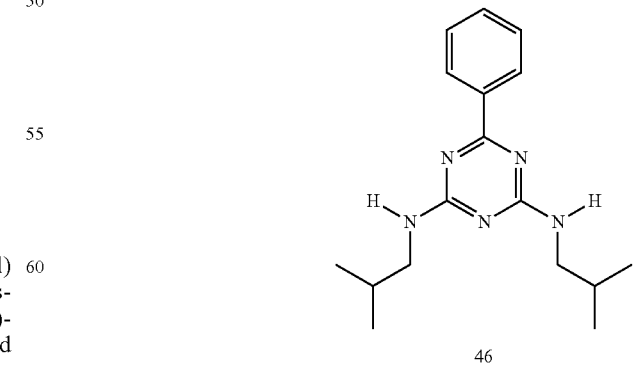

46

N$^2$,N$^4$-Diisobutyl-6-phenyl-1,3,5-triazine-2,4-diamine (46). A solution of phenylmagnesium bromide, prepared from bromobenzene (0.5 mL, 4.75 mmol) and magnesium turnings (0.29 g) in dry diethyl ether, was added to a solution of cyanuric chloride (1.2 g, 6.52 mmol) dissolved in dry diethyl ether at 0° C. The mixture allowed to warm to room temperature and stirring was continued (16 h). Diisopropyl ethylamine (3.5 mL, 3 eq) was then added followed by isobutylamine (2.0 mL, 3 eq) resulting in a precipitate. The solvent was then removed from the reaction mixture, the resulting residue was then poured into chloroform 200 mL, washed with water, 0.7M HCl and dried over sodium sulfate. Removal of the drying agent and solvent gave a brown residue which was flash-chromatographed on silica gel (hexane/ethyl acetate, 19:1) to give 46 (90 mg, <5%) as a white solid. The $^1$H and $^{13}$CNMR data were consistent with the expected product,

EXAMPLE 9

Testing of Compounds for Inhibition of *P. gingivalis* Adherence to Streptococci Compounds 25, 27a, 34, 35 and 42 were tested to determine if they inhibited *P. gingivalis* adherence to streptococci using a two species biofilm culture model. Compounds of the invention (e.g. compounds of formula I) can also be tested using this method. A mid-exponential phase culture of *S. gordonii* DL-1 was harvested by centrifugation and the cells were suspended in phosphate buffered saline (PBS) at a density of $10^9$ cfu/ml. A 1 ml aliquot was labeled with hexidium iodide (30 µM) for 15 minutes with gentle shaking. After washing three times with PBS, streptococci were suspended in growth medium and 100 µl was added to a 12 well microtiter plate (Grace Bio-Labs) and incubated anaerobically for 24 hrs.

*P. gingivalis* cells from an exponential culture were washed with PBS and labeled by reacting with 4 µg/ml carboxyfluorescein-succinyl ester for 30 minutes at 4° C. After washing three times with PBS, the cells were suspended in PBS at a density of 2×10$^7$ cfu/ml. The test compounds were dissolved in absolute ethanol to a final concentration of 30 mM and each was diluted into 100 µl *P. gingivalis* to final concentrations of 5, 20 or 60 µM and incubated for 30 minutes. After removal of unbound streptococci from the micotiter plate, *P. gingivalis* samples were then added to each well and incubated anaerobically for 24 hrs. A control well contained *P. gingivalis* that was pre-incubated with PBS alone.

Adherence of *P. gingivalis* to streptococci was analyzed using confocal laser scanning microscopy on an Olympus FluoView 500 inverted confocal microscope. Image stacks were acquired using Olympus FluoView software and rendered into 3 dimensional projections using Volocity Image Analysis software, where *S. gordonii* is depicted in red and *P. gingivalis* is shown in green/yellow. Compound 27a showed a dose dependent inhibition of *P. gingivalis* adherence and completely blocked adherence at a concentration of 60 Compound 42 showed a dose dependent inhibition and completely inhibited adherence even at the 20 µM concentration. Compound 34 significantly reduced *P. gingivalis* adherence at 5 µM and completely blocked adherence at a concentration of 20 µM. Compound 25 completely inhibited *P. gingivalis* adherence at the 5 µM concentration point. Compound 35 significantly reduced adherence at 20 µM and completely blocked *P. gingivalis* adherence at 60 µM. Compound 46 reduced *P. gingivalis* adherence to streptococci by 25% at 25 µM and by approximately 60% at 50 µM.

EXAMPLE 10

Synthesis of Final Compounds

The following compounds can be prepared from the intermediate compounds described in the examples above (and by methods described herein) and by the "click" chemistry methods described herein and in Scheme 6.

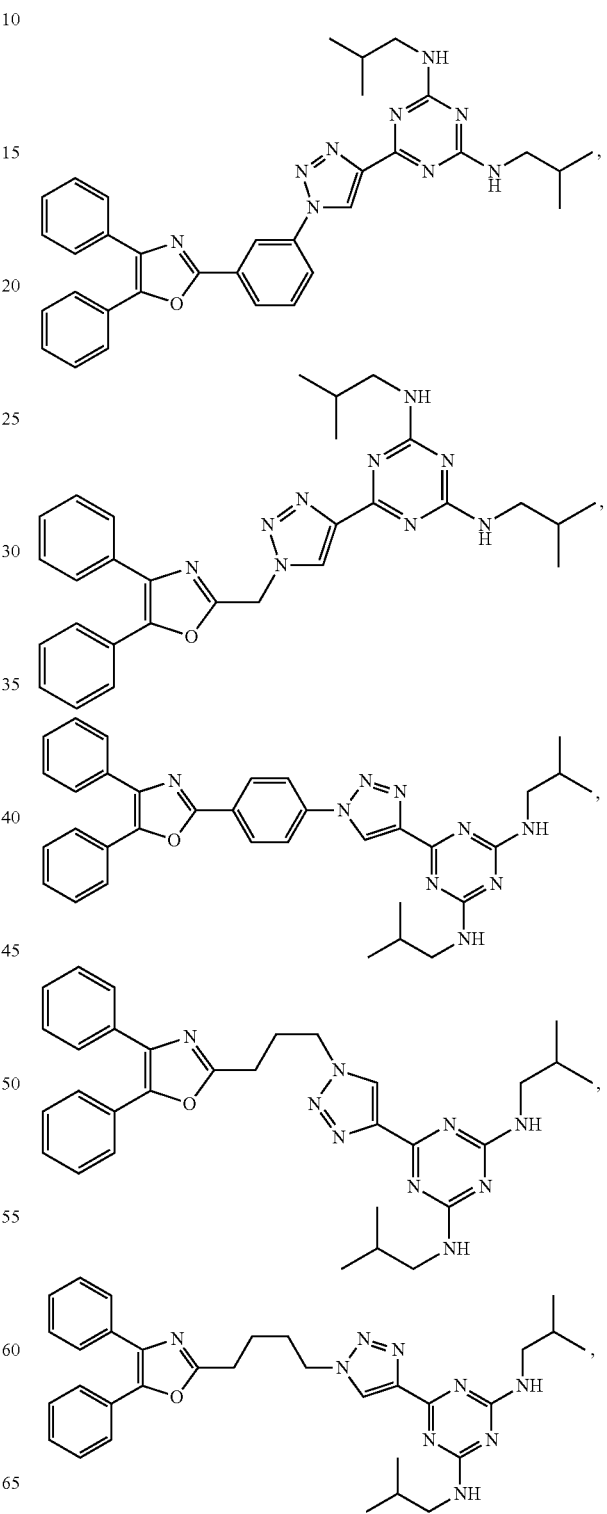

-continued

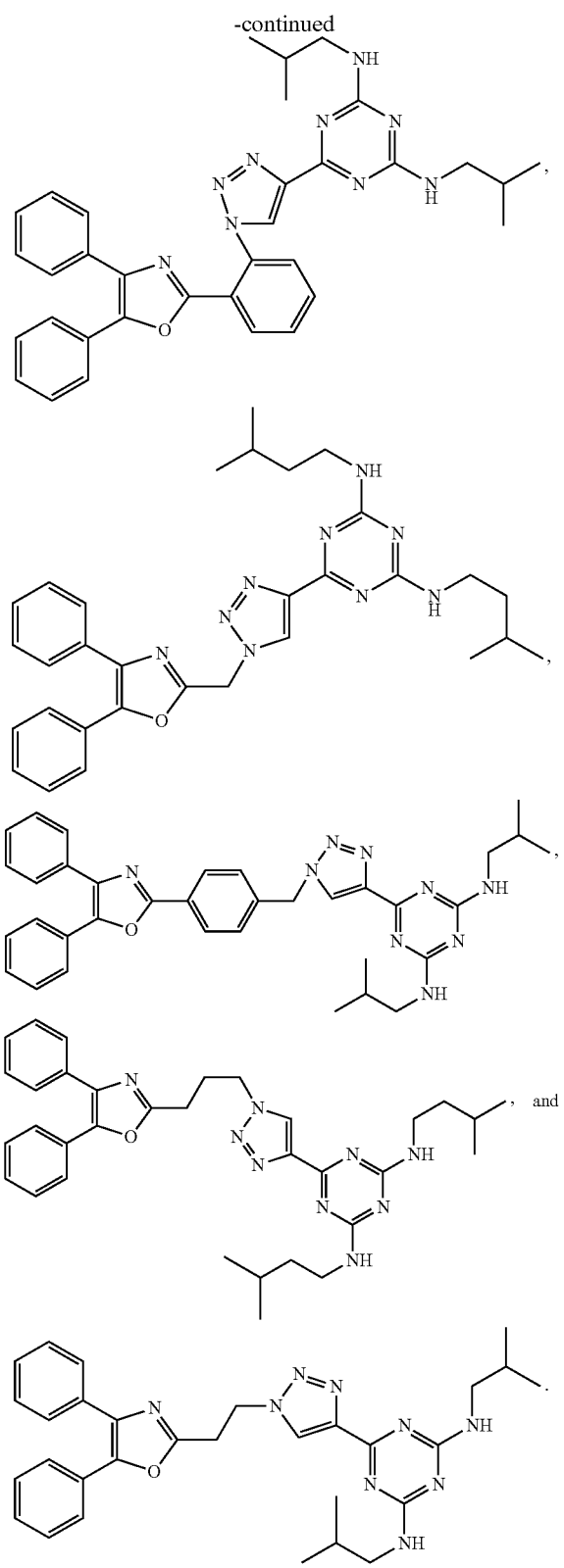

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:
1. A compound of formula I:

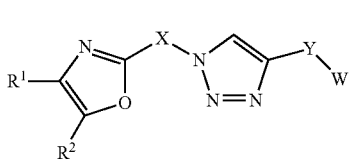

wherein:
X is —($C_1$-$C_8$)alkyl-, aryl or -aryl($C_1$-$C_8$)alkyl-;
Y is —($C_1$-$C_8$)alkyl- or absent;
W is heteroaryl, ($C_3$-$C_7$)carbocycle or aryl wherein any heteroaryl, ($C_3$-$C_7$)carbocycle or aryl of W is optionally substituted with one or more $Z^1$ groups;
$R^1$ is ($C_1$-$C_8$)alkyl, ($C_2$-$C_8$)alkenyl, ($C_2$-$C_8$)alkynyl or aryl, wherein aryl is optionally substituted with one or more groups selected from ($C_1$-$C_8$)alkyl, ($C_2$-$C_8$)alkenyl, ($C_2$-$C_8$)alkynyl, ($C_3$-$C_7$)carbocycle, halo($C_1$-$C_3$)alkyl, —CN, $NO_2$, halogen, —$OR_a$, —$SR_a$, —$S(O)_2NR_bR_c$, —$NR_bR_c$, —$NR_aCOR_d$, —$C(O)R_a$, —$C(O)OR_a$ or —$C(O)NR_bR_c$;
$R^2$ is ($C_1$-$C_8$)alkyl, ($C_2$-$C_8$)alkenyl, ($C_2$-$C_8$)alkynyl or aryl, wherein aryl is optionally substituted with one or more groups selected from ($C_1$-$C_8$)alkyl, ($C_2$-$C_8$)alkenyl, ($C_2$-

C$_8$)alkynyl, (C$_3$-C$_7$)carbocycle, halo(C$_1$-C$_3$)alkyl, —CN, NO$_2$, halogen, —OR$_e$, —SR$_e$, —S(O)$_2$NR$_f$R$_g$, —NR$_f$R$_g$, —NR$_e$COR$_h$, —C(O)R$_e$, —C(O)OR$_e$ or —C(O)NR$_f$R$_g$;

each R$_a$ is independently selected from H, (C$_1$-C$_8$)alkyl, (C$_2$-C$_8$)alkenyl, (C$_2$-C$_8$)alkynyl, (C$_3$-C$_7$)carbocycle or aryl;

R$_b$ and R$_c$ are each independently selected from H, (C$_1$-C$_8$)alkyl, (C$_2$-C$_8$)alkenyl, (C$_2$-C$_8$)alkynyl, (C$_3$-C$_7$)carbocycle or aryl, or R$_b$ and R$_c$ together with the nitrogen to which they are attached form a 5, 6 or 7-membered heterocycle;

R$_d$ is independently selected from (C$_1$-C$_8$)alkyl, (C$_2$-C$_8$)alkenyl, (C$_2$-C$_8$)alkynyl, (C$_3$-C$_7$)carbocycle or aryl;

each R$_e$ is independently selected from H, (C$_1$-C$_8$)alkyl, (C$_2$-C$_8$)alkenyl, (C$_2$-C$_8$)alkynyl, (C$_3$-C$_7$)carbocycle or aryl;

R$_f$ and R$_g$ are each independently selected from H, (C$_1$-C$_8$)alkyl, (C$_2$-C$_8$)alkenyl, (C$_2$-C$_8$) alkynyl, (C$_3$-C$_7$)carbocycle or aryl, or R$_f$ and R$_g$ together with the nitrogen to which they are attached form a 5, 6 or 7-membered heterocycle;

R$_h$ is selected from (C$_1$-C$_8$)alkyl, (C$_2$-C$_8$)alkenyl, (C$_2$-C$_8$) alkynyl, (C$_3$-C$_7$)carbocycle or aryl;

each Z$^1$ is independently selected from (C$_1$-C$_8$)alkyl, (C$_2$-C$_8$)alkenyl, (C$_2$-C$_8$)alkynyl, aryl, heteroaryl, —OR$_i$, —NR$_j$R$_k$ or —NR$_i$COR$_m$, wherein any aryl or heteroaryl of Z$^1$ is optionally substituted with one or more (C$_1$-C$_8$)alkyl;

each R$_i$ is selected from H or (C$_1$-C$_8$)alkyl;

R$_j$ and R$_k$ are each independently selected from H or (C$_1$-C$_8$)alkyl;

R$_m$ is (C$_1$-C$_8$)alkyl optionally substituted with one or more —N(R$_n$)$_2$ or —N(R$_n$)$_3$$^+$Q$^-$ wherein Q$^-$ is halogen; and each R$_n$ is independently H or (C$_1$-C$_8$)alkyl;

or a salt thereof.

2. The compound of claim 1, wherein X is phenyl or —(C$_1$-C$_8$)alkyl-.

3. The compound of claim 1, wherein W is pyrimidinyl, triazinyl, cyclohexyl or benzoxazolyl, wherein any pyrimidinyl, triazinyl, cyclohexyl or benzoxazolyl of W is optionally substituted with one or more Z$^1$ groups.

4. The compound of claim 1, wherein each Z$^1$ is independently selected from (C$_1$-C$_8$)alkyl, —NH(C$_1$-C$_8$)alkyl, —NHCO—(C$_1$-C$_8$)alkyl-N$^+$Me$_3$Q$^-$, aryl or heteroaryl, wherein any aryl or heteroaryl of Z$^1$ is optionally substituted with one or more (C$_1$-C$_8$)alkyl and wherein Q$^-$ is halogen.

5. The compound of claim 1, wherein, W is:

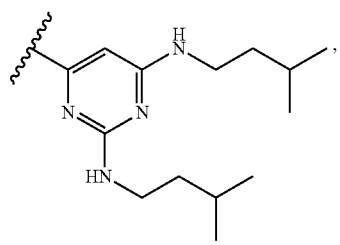

-continued

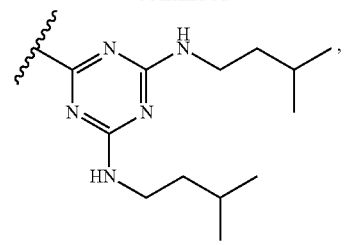

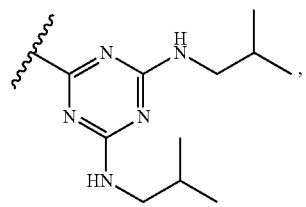

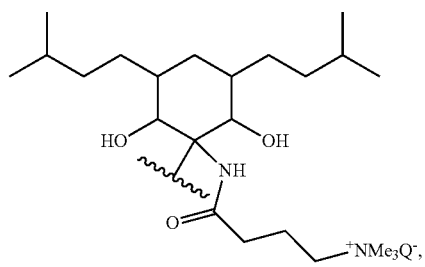

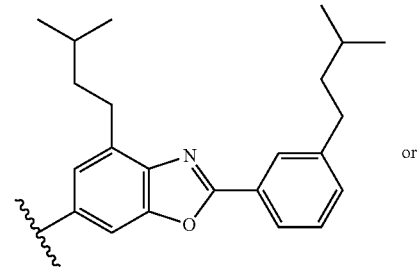

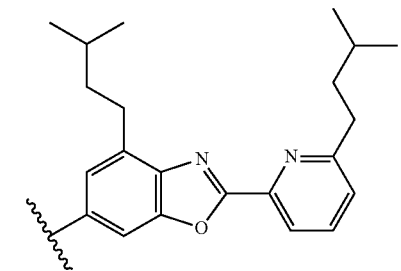

6. The compound of claim 1, wherein R$^1$ is (C$_1$-C$_8$)alkyl or aryl, wherein aryl is optionally substituted with one or more groups selected from (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_a$, —NR$_b$R$_c$, —NR$_a$COR$_d$, —C(O)R$_a$, —C(O)OR$_a$ or —C(O)NR$_b$R$_c$.

7. The compound of claim 1, wherein R$^2$ is (C$_1$-C$_8$)alkyl or aryl, wherein aryl is optionally substituted with one or more groups selected from (C$_1$-C$_8$)alkyl, (C$_2$-C$_8$)alkenyl, (C$_2$-C$_8$)alkynyl, (C$_3$-C$_7$)carbocycle, halo(C$_1$-C$_3$)alkyl, —CN, NO$_2$, halogen, —OR$_e$, —NR$_f$R$_g$, —NR$_e$COR$_h$, —C(O)R$_e$, —C(O)OR$_e$ or —C(O)NR$_f$R$_g$.

8. The compound of claim 1, wherein Y is absent.

9. The compound of claim 1 selected from:
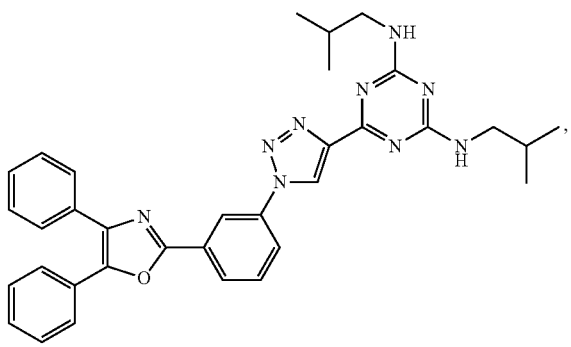
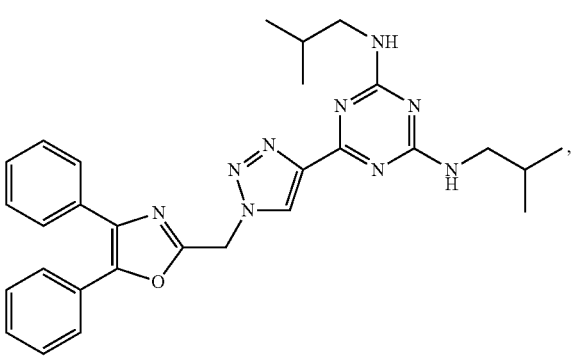
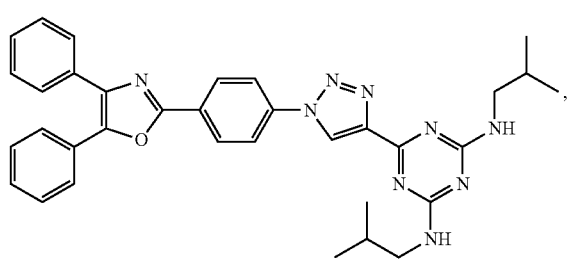
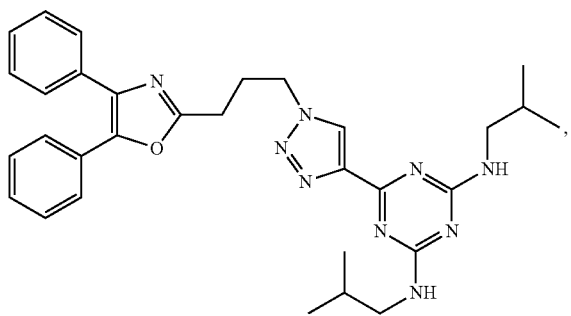
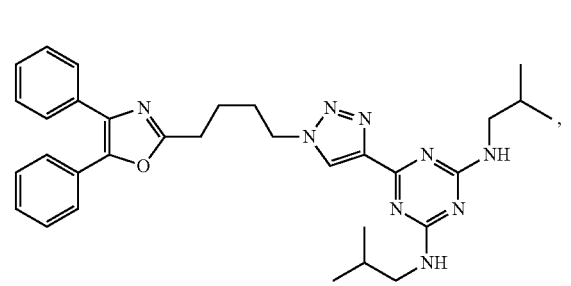
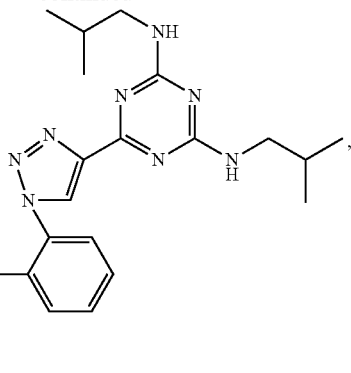
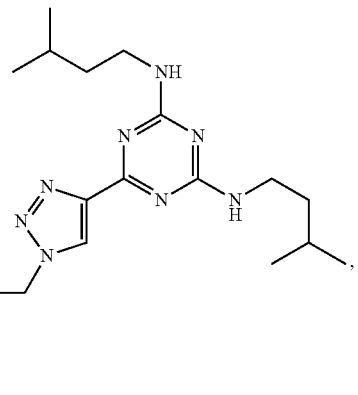
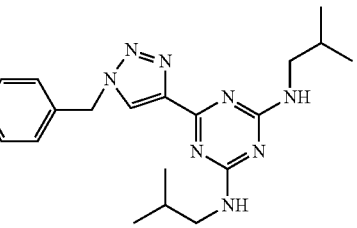
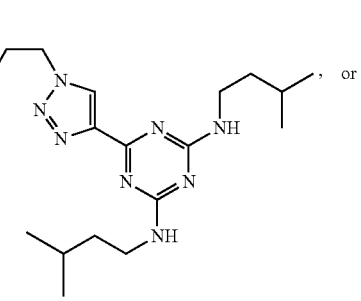
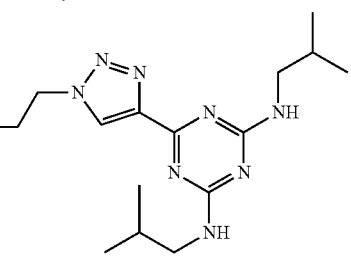
and salts thereof.
10. A composition comprising a compound of formula I as described in claim 1 or a salt thereof and a physiologically acceptable carrier.

11. A therapeutic method for preventing or treating a pathological condition or symptom in a mammal in need of such therapy, wherein an antibiotic activity against *P. gingivalis* is desired, comprising administering to the mammal an effective amount of pharmaceutically acceptable salt thereof or a composition of claim 10.

12. A therapeutic method for preventing or treating a pathological condition or symptom in a mammal in need of such therapy, wherein anti-*P. gingivalis* biofilm formation is desired, comprising administering to the mammal an effective amount of a pharmaceutically acceptable salt thereof or a composition of claim 10.

13. A method to treat a *P. gingivalis* microbial infection in a mammal comprising administering a therapeutically effective amount of a composition of claim 10 to the mammal.

14. A method of preventing the adhesion of *P. gingivalis* bacteria on a solid substrate comprising contacting the solid substrate with a compound of formula I as described in claim 1 or a salt thereof.

15. A method of preventing the formation of a biofilm of *P. gingivalis* bacteria in vivo comprising contacting a tissue surface with a composition of claim 10.

16. A solution comprising a solvent, a polymer dissolved in the solvent and a compound of formula I as described in claim 1 or a salt thereof.

17. A method for manufacturing a solid substrate coated with a compound of formula I comprising applying to the solid substrate a layer which is a solid composite of polymer and a compound of formula I as described in claim 1 or a salt thereof, wherein the first layer is applied by the steps of:
 (a) applying to the solid substrate a solution which includes a solvent, a polymer dissolved in the solvent and a compound of formula I dispersed in the solvent; and
 (b) evaporating the solvent to form a composite of polymer and compound of formula I.

18. The method of claim 17, wherein the polymer is a bioabsorbable polymer.

19. A coated device comprising:
 (a) a solid substrate; and
 (b) a solid composite of a compound of formula I as described in claim 1 or a salt thereof and a therapeutic substance in an adherent layer on the solid substrate.

20. The device according to claim 19, wherein the solid substrate has a polymeric surface comprising a polymer that is a bioabsorbable polymer or a biostable polymer.

* * * * *